United States Patent
Onouchi

(10) Patent No.: US 9,980,683 B2
(45) Date of Patent: May 29, 2018

(54) ANALOG/DIGITAL CONVERSION SYSTEM, X-RAY CT APPARATUS, AND MEDICAL IMAGE IMAGING APPARATUS

(71) Applicant: Hitachi, Ltd., Tokyo (JP)

(72) Inventor: Masafumi Onouchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days. days.

(21) Appl. No.: 15/504,259

(22) PCT Filed: Aug. 5, 2015

(86) PCT No.: PCT/JP2015/072263
§ 371 (c)(1),
(2) Date: Feb. 15, 2017

(87) PCT Pub. No.: WO2016/027677
PCT Pub. Date: Feb. 25, 2016

(65) Prior Publication Data
US 2017/0258415 A1 Sep. 14, 2017

(30) Foreign Application Priority Data
Aug. 18, 2014 (JP) .................................. 2014-166144

(51) Int. Cl.
*H03M 1/06* (2006.01)
*A61B 6/03* (2006.01)
*H03M 1/12* (2006.01)

(52) U.S. Cl.
CPC ........... *A61B 6/035* (2013.01); *H03M 1/1245* (2013.01)

(58) Field of Classification Search
CPC ............................ H03M 1/1245; A61B 6/085

USPC .......................................................... 341/122
See application file for complete search history.

(56) References Cited

U.S. PATENT DOCUMENTS

2006/0250291 A1* 11/2006 Lyden ..................... H03M 1/08
341/155
2012/0071122 A1* 3/2012 Akita ................... G11C 27/024
455/130

FOREIGN PATENT DOCUMENTS

JP 2008541576 A 11/2008
JP 2013247570 A 12/2013

OTHER PUBLICATIONS

International Search Report received for International Patent Application No. PCT/JP2015/072263, dated Sep. 15, 2015.

* cited by examiner

*Primary Examiner* — Lam T Mai

(57) ABSTRACT

In order to provide a highly precise analog/digital conversion system in which an output error of an AD converter is small, sampling is performed at a certain sampling period S from the start time of a measurement period TL to the (N−1)-th sampling when the measurement period TL does not correspond to the sampling period S multiplied by the number of samplings N, the N-th sampling is performed at a timing when a time interval between the (N−1)-th sampling and the N-th sampling is equal to the sampling period S multiplied by a predetermined coefficient k, and the k value is set to a non-integer optimum value evaluated in advance in accordance with the N value in order to minimize an error of the detection value of the AD converter.

14 Claims, 28 Drawing Sheets

(a)　　　　　　　　(b)

MAIN SIGNAL ACTION

| SCANNING NUMBER (VIEW NUMBER) | MEASUREMENT PERIOD (msec) | DIFFERENCE FROM IDEAL MEASUREMENT PERIOD |
|---|---|---|
| 1 | 0.8583330 | 2.999959% |
| 2 | 0.8583320 | 2.999836% |
| 3 | 0.8583302 | 2.999630% |
| 4 | 0.8583279 | 2.999342% |
| 5 | 0.8583248 | 2.998972% |
| 6 | 0.8583210 | 2.998520% |
| ⋮ | ⋮ | ⋮ |
| 300 | 0.8333333 | 0.000000% |
| ⋮ | ⋮ | ⋮ |
| 600 | 0.8083333 | -3.000000% |
| ⋮ | ⋮ | ⋮ |
| 900 | 0.8333333 | 0.000000% |
| ⋮ | ⋮ | ⋮ |
| 1200 | 0.858333 | 3.000000% |

| SCANNING NUMBER (VIEW NUMBER) | MEASUREMENT PERIOD (msec) | DIFFERENCE FROM IDEAL MEASUREMENT PERIOD |
|---|---|---|
| 1 | 0.3576389 | 2.999993% |
| 2 | 0.3576388 | 2.999971% |
| 3 | 0.3576387 | 2.999936% |
| 4 | 0.3576385 | 2.999886% |
| 5 | 0.3576383 | 2.999822% |
| 6 | 0.3576380 | 2.999743% |
| ⋮ | ⋮ | ⋮ |
| 720 | 0.3472222 | 0.000000% |
| ⋮ | ⋮ | ⋮ |
| 1440 | 0.3368056 | -3.000000% |
| ⋮ | ⋮ | ⋮ |
| 2160 | 0.3472222 | 0.000000% |
| ⋮ | ⋮ | ⋮ |
| 2880 | 0.3576389 | 3.000000% |

2,880TH SCANNING (360 DEGREES)  FIRST SCANNING (0.125 DEGREES)

2,160TH SCANNING (270 DEGREES)                    7,200TH SCANNING (90 DEGREES)

1,440TH SCANNING (180 DEGREES)

ANALOG/DIGITAL CONVERSION SYSTEM, X-RAY CT APPARATUS, AND MEDICAL IMAGE IMAGING APPARATUS

CROSS-REFERENCE TO RELATED APPLICATIONS

This application is a national phase claiming the benefit of and priority to International Patent Application No. PCT/JP2015/072263, entitled "ANALOG/DIGITAL CONVERSION SYSTEM, X-RAY CT APPARATUS, AND MEDICAL IMAGE CAPTURE APPARATUS", filed Aug. 5, 2015, which claims priority to Japanese Patent Application No. 2014-166144, entitled "ANALOG/DIGITAL CONVERSION SYSTEM, X-RAY CT APPARATUS, AND MEDICAL IMAGE CAPTURE APPARATUS", filed Aug. 18, 2014, which are hereby incorporated by reference in their entireties.

TECHNICAL FIELD

The present invention relates to an analog/digital converter system having low noise and a wide dynamic range.

BACKGROUND ART

It is desirable that low noise and a wide dynamic range are compatible as characteristics of an analog/digital conversion circuit (AD conversion circuit) to be used in a medical image diagnostic apparatus such as a CT (Computed Tomography) scanner. Specifically, a radiation transmitted through a low-density body part is very high, and it is said that the AD conversion circuit with a 120-dB dynamic range is required to convert analog signals detecting the radiation into digital signals. However, on the other hand, a radiation transmitted through a bone or a large object is very low, and it is required that noise of the AD conversion circuit is extremely low.

In order to solve these two problems, Patent Literature 1 and Patent Literature 2 disclose an analog/digital conversion circuit that integrates output of a detector that detected a radiation with an integral amplification circuit using an AD converter whose dynamic range is limited, an integration circuit, and a comparator and converts the output of the integral amplification circuit into digital signals by performing sampling with the AD converter.

The AD converter samples output of the integration circuit a plurality of times at a predetermined sampling period during a predetermined measurement period. When the comparator detects that output of the integral amplification circuit reaches a predetermined maximum voltage level, the output of the integral amplification circuit is reset to a predetermined minimum voltage level. This configures a circuit capable of converting a high-intensity radiation into digital signals with the AD converter whose dynamic range is limited. In Patent Literature 1, provided are an isolation circuit isolating the integral amplification circuit from the detector during a sampling event of the AD converter, an isolation circuit isolating the integral amplification circuit from a feedback capacitor when the integral amplification circuit is reset, and the like in order to reduce noise of the AD converter. Hence, disclosed is a technique capable of converting a low-intensity radiation into digital signals with low noise.

CITATION LIST

Patent Literature

PTL 1: JP-T-2008-541576
PTL 2: U.S. Pat. No. 7,136,005

SUMMARY OF INVENTION

Technical Problem

It is known that an error occurs between detected values in an AD converter when a voltage signal to be input is higher than a voltage threshold value. The process in which such a measurement error occurs can be explained by an error caused by several circuit operations shown as follows. For example, as illustrated in FIG. 1(a), when a voltage signal to be input gets closer to the maximum input range estimated during the design is higher than a voltage threshold value, decreasing or increasing characteristics (V025 or V026 of FIG. 1(a)) are generated in an input offset voltage of a comparator included in the AD converter, which occurs an error between detection values of the AD converter.

As another phenomenon, it is thought that an error of the detection value of sampling S017 is increased by applying noise higher than usual to a circuit because large voltage fluctuation is caused in resetting an electric potential S017' that exceeds the voltage threshold value greatly to S017. Even in a case where this phenomenon occurs, it can be thought that the detection value of sampling S017' have a large measurement error.

Although measurement errors of the AD converter occur due to various circuit operations as described above, the description will be made using a simplified case where an input offset voltage of the AD converter changes and the measurement error becomes larger as an input voltage into the AD converter gets closer to an end of the estimated range in the description of the present application.

Although a state where a measurement error of the AD converter is increased in the increasing direction of the voltage (from V022 to V023) is illustrated in FIG. 1(a) in order to simplify the description, the measurement error of the AD converter can be increased also in the decreasing direction of the voltage (from V022 to V021) in the actual circuit characteristics.

In a circuit that performs sampling a plurality of times during one measurement period TL using an AD converter having such a circuit characteristics similarly to an analog/digital conversion circuit suggested in Patent Literatures 1 and 2, the input voltage of the next sampling S017' exceeds the voltage threshold value by a value corresponding to one sampling period S1 when the input voltage (output of an integral amplification circuit) in certain sampling S016 is slightly lower than the voltage threshold value as illustrated in FIG. 1(b). After the AD converter detects the voltage of the sampling S017', the output of the integral amplification circuit is reset. Therefore, the detection value of the sampling S017' of the AD converter includes an error of fluctuation of the input offset voltage.

In case of using the analog/digital conversion circuit for converting output signals from the X-ray detector of an X-ray CT apparatus into digital signals, a measurement period TL corresponds to view intervals and is determined by the system configuration and imaging conditions (such as a rotation speed) of the X-ray CT apparatus. On the other hand, a sampling period of the AD converter is determined by operational specifications of ASIC. Hence, there can be a case where the measurement period does not correspond to the sampling period of the AD converter multiplied by the number of samplings.

In case of the X-ray CT apparatus, there can also be a case where unevenness occurs to the view intervals and the measurement period is extended due to uneven rotation of a rotating disk mounting the X-ray detector and the like. Thus, a technique for extending and contracting any of the sampling intervals is required to perform sampling a predetermined number of times during the measurement period when the measurement period is not an integral multiple of the sampling period and when the measurement period is extended or contracted.

In case of extending one of sampling periods in such a state, an input voltage at sampling S027' exceeds a voltage threshold value by a value corresponding to an extended sampling period SL when an extended sampling interval (between S026 and S027') includes a timing of reaching the voltage threshold value as illustrated in FIG. 2. Therefore, a detection value of the sampling S027' of the AD converter includes an error larger than a detection value of the sampling S017' of FIG. 1.

The purpose of the present invention is to provide a highly precise analog/digital conversion system in which an output error of the AD converter is small.

Solution to Problem

The analog/digital conversion system related to the present invention performs sampling at a certain sampling period S from the start time of a measurement period to the (N−1)-th sampling when the measurement period does not correspond to the sampling period multiplied by the number of samplings, and the N-th sampling is performed at a timing when a time interval between the (N−1)-th sampling and the N-th sampling is equal to the sampling period S multiplied by a predetermined coefficient k. At this time, the k value is set to a non-integer optimum value evaluated in advance in accordance with the N value in order to minimize an error of the detection value of the AD converter.

Advantageous Effects of Invention

The present invention can minimize a detection value error of the AD converter and provide a highly precise analog/digital conversion system.

DESCRIPTION OF EMBODIMENTS

The embodiments of the present invention will be described.

<<First Embodiment>>

The AD conversion system of the present embodiment performs sampling at a certain sampling period S from the start time of a measurement period to the (N−1)-th sampling when a specified measurement period does not correspond to the sampling period multiplied by the number of samplings, and the N-th sampling is performed at the same time as when the measurement period ends and at a timing when a time interval between the (N−1)-th sampling and the N-th sampling is equal to the sampling period S multiplied by a predetermined coefficient k. The inventors found that a detection value error of the AD converter can be minimized simultaneously by setting the k value to an optimum value evaluated in advance in accordance with the N value. An analog-digital (AD) conversion system realizing the above will be described in the following using FIG. 3 and the like.

Figure 3:
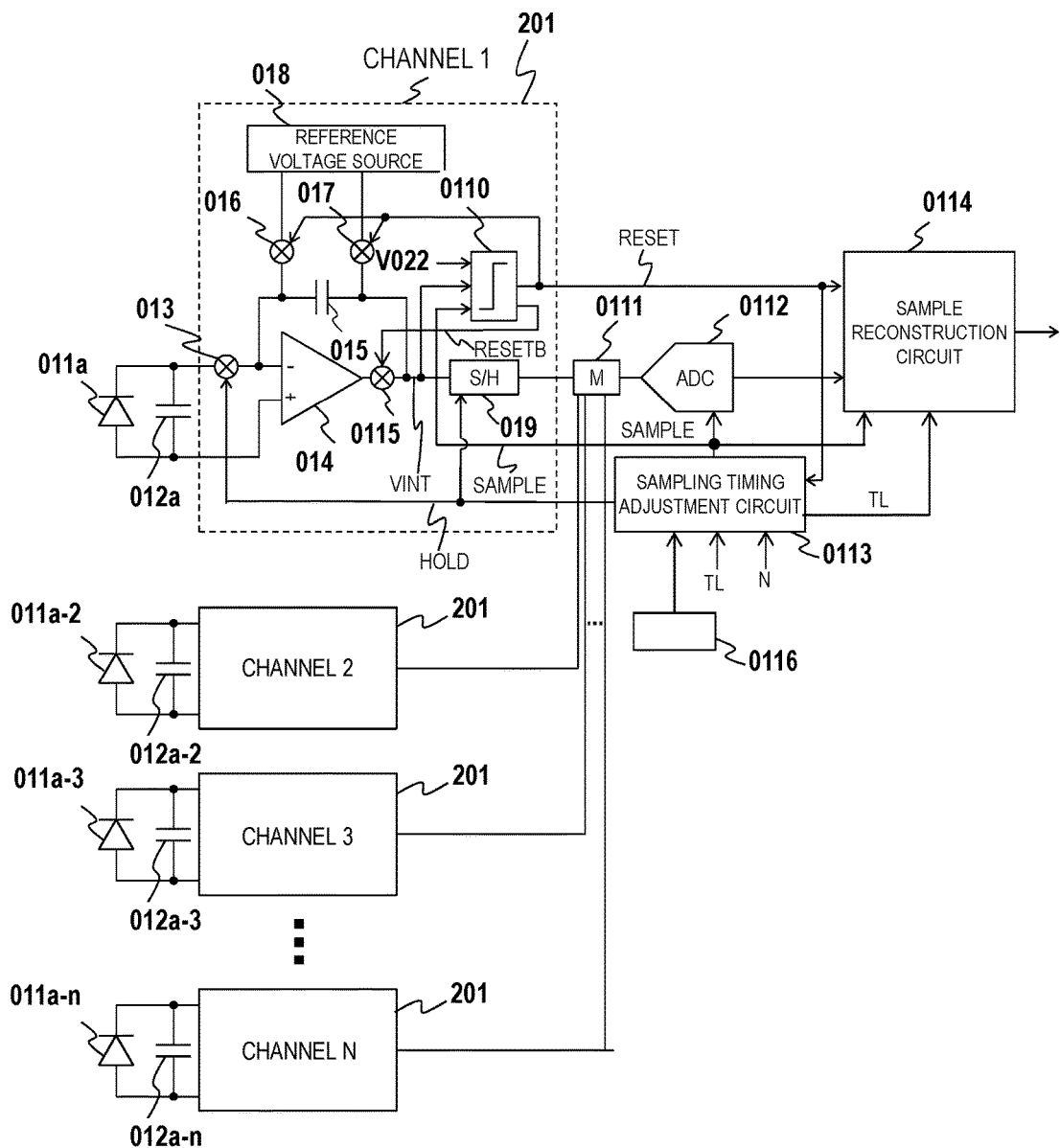
FIG. 3 is a block diagram of an AD conversion system of a first embodiment.
Figure 4:
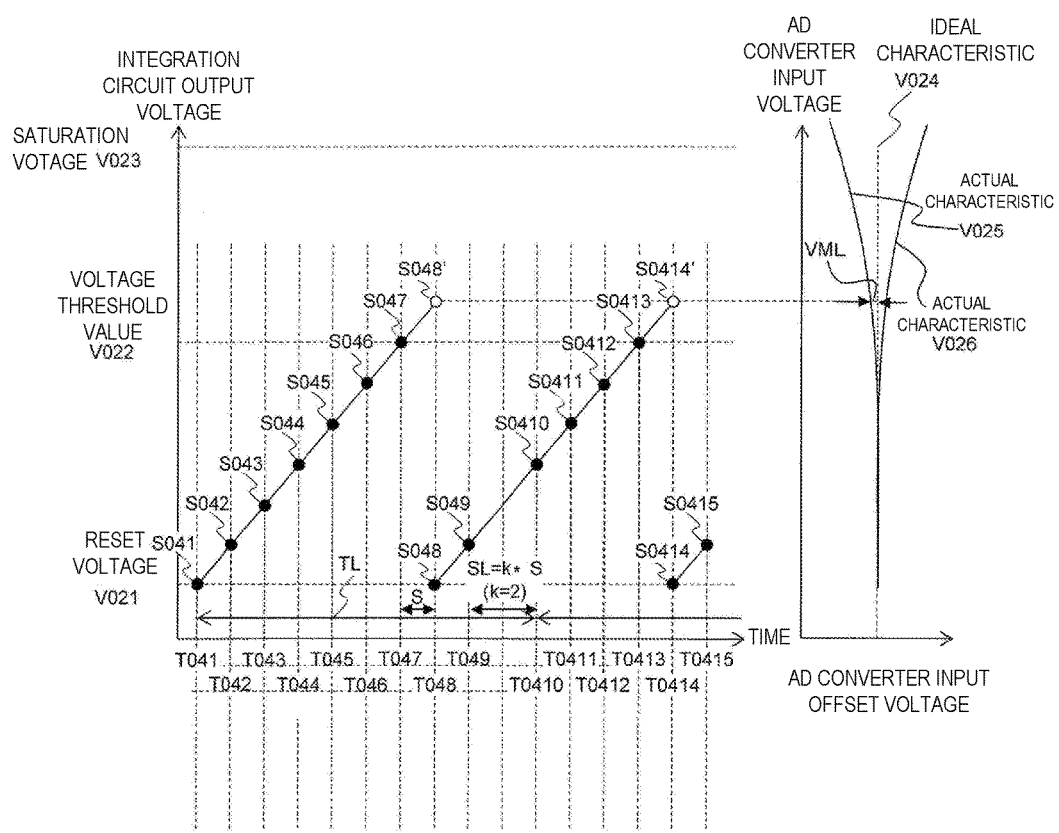
FIG. 4 illustrates a case where the extended sampling interval SL of the AD conversion system is an integral multiple of a sampling interval S.

That is, the AD conversion system of the first embodiment includes the AD converter 0112, reset circuits (0110 and 0113), and a timing circuit (hereinafter, referred to as a sampling timing adjustment circuit) 0113 as illustrated in FIG. 3. As illustrated in FIG. 4, the AD converter 0112 repeats operations of sampling analog signals output from analog circuits 011a and 012a by the number of samplings N each time a measurement period TL elapses within the specified measurement period TL.

When a signal value sampled by the AD converter 0112 exceeds a predetermined maximum voltage (V022), the reset circuits (0110 and 0113) repeat operations of lowering an analog signal voltage to a predetermined minimum voltage to input in the AD converter 0112 each time the sampled signal value exceeds the maximum voltage (V022). Additionally, the sampling timing adjustment circuit 0113 instructs the AD converter 0112 on a timing of sampling the analog signals.

Simultaneously, the sampling timing adjustment circuit (0113) instructs a timing of sampling as described below in a case where a difference (SL) is generated between the measurement period TL and a net measurement period to be calculated from the sampling period S multiplied by the number of samplings N as illustrated in FIG. 4 in order to reduce an error VML between detection values of the AD converter 0112 so as to be a value closer to the minimum value.

Figure 5:
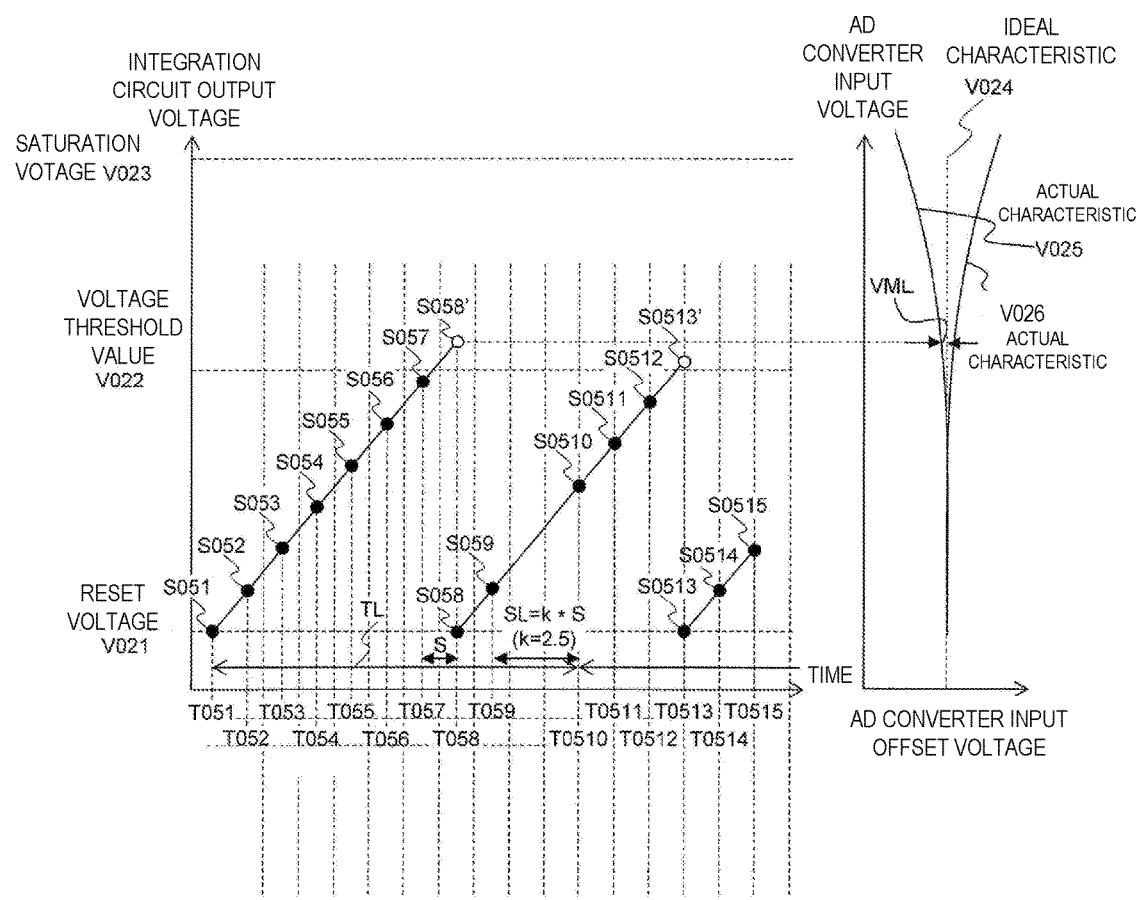
FIG. 5 illustrates the sampling intervals S and SL as well as the detection error VML of the AD conversion system of the first embodiment.

That is, the sampling timing adjustment circuit (0113) provides the instruction at a predetermined sampling period S from the start time of the measurement period TL to the (N−1)-th sampling (S059) as illustrated in FIG. 5 and instructs the N-th sampling (S0510) at the same time as when the measurement period TL ends and at a timing when a time interval SL between the (N−1)-th sampling and the N-th sampling is equal to the sampling period S multiplied by a predetermined coefficient k (SL=k*S). The above is similar also to the next measurement period (after time T510).

A predetermined value is used as the coefficient k. For example, a value satisfying (M+0.3)<=k<=(M+0.5) (M is a non-negative integer) is used for k. In other words, used is a value closer to a half-integer multiple of k.

Hence, the sampling timing adjustment circuit (0113) can execute sampling so that analog signals to be input in the AD converter 0112 suppress an excess of the maximum voltage (V022) as illustrated in FIG. 5.

Thus, because sampling can be performed so as to suppress the excess of the maximum voltage (V022) according to the first embodiment, as illustrated in FIG. 5, a difference between the input voltage in the AD converter 0112 and the maximum voltage (V022) at sampling S058' and sampling S0513' is smaller than that in a case where the time interval SL is an integral multiple of the sampling interval S as illustrated in FIG. 4. Hence, an error VML of the detection value of the AD converter 0112 in case of FIG. 5 of the present embodiment is smaller than that in case of FIG. 4.

Next, an optimal value of the above coefficient k will be further described in detail. As a model case where a measurement period TL is not an integral multiple of a sampling period S, provided an example when a sampling interval between (N−1)-th sampling and N-th sampling is extended to SL(>)S after performing sampling at the sampling period S until (N−1)-th sampling S049 as illustrated in FIG. 4 and the N-th sampling S0410 corresponds to the end time of the measurement period TL.

In this case, as illustrated in FIG. 4, an error VML of the detection value of the AD converter 0112 becomes larger because detection electric potentials of samplings S048' and S0414' periodically exceeds the maximum voltage (hereinafter, referred to as a voltage threshold value) V022 at a voltage difference corresponding to the sampling period S (S048' to S047 or S0414' to S0413). This is caused by that an excess of the voltage threshold value V022 is always generated at the same timing because the coefficient k is equal to an integer 2 in FIG. 4.

Figure 6:
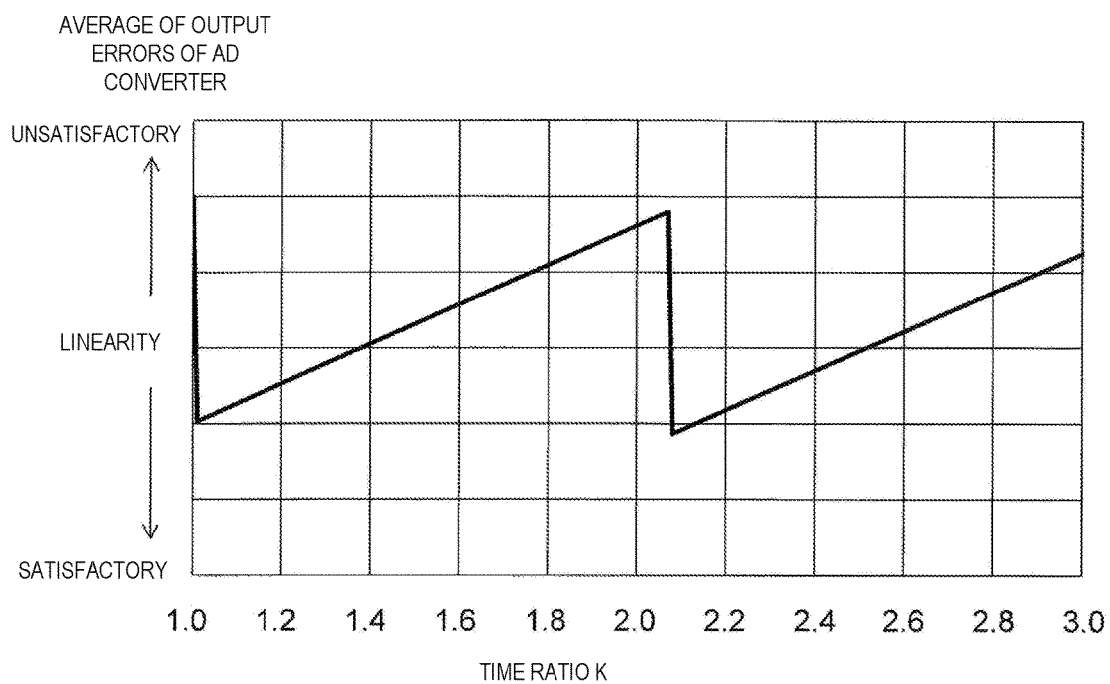
FIG. 6 is a graph illustrating a relationship between a time ratio k and a change amount of an output error of an AD converter 0112 of the AD conversion system of the first embodiment.

Therefore, the coefficient k is shifted from an integer in order to averagely suppress an excess of the voltage threshold value V022 of sampling. FIG. 6 illustrates calculation of a relationship between the coefficient k and an output error of the AD converter for an input amount at which just one reset is generated per seven samplings (equivalent to FIG. 4) in case of the number of samplings N=10. It is presumed that the excess of the voltage threshold value V022 fluctuates due to insertion of an extended period SL to simplify the calculation, and the calculation is performed supposing that the detection error of the AD converter 0112 is proportional to an excess of the sampled voltage to the voltage threshold value V022.

Although it is found that the coefficient k suppressing an output error of the AD converter includes a plurality of minimum points such as 1.1, 2.1, x.1 (x is an integer) from FIG. 6, the output error is abruptly increased when the coefficient k is even a little smaller than the minimum points. A measurement error can be stably suppressed by practically setting the coefficient k as M+0.3<=k<=M+0.5 (M is a non-negative integer) such as 1.3 to 1.5, 2.3 to 2.5, and the like.

Figure 7:
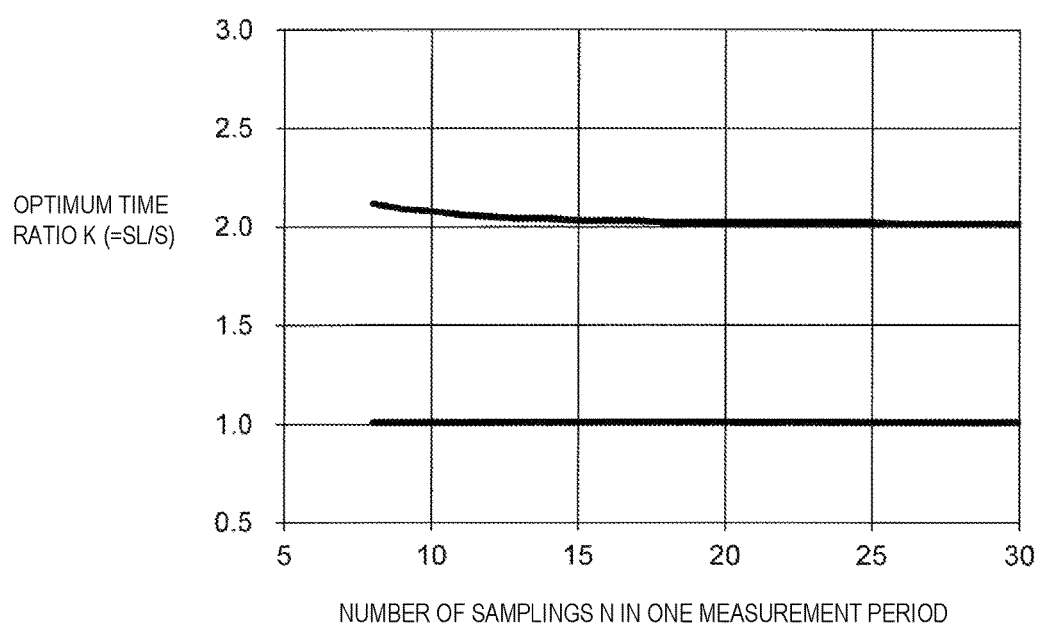
FIG. 7 is a graph illustrating the time ratio k that suppresses detection errors for each number of samplings N in the AD conversion system of the first embodiment.

FIG. 7 shows a result of evaluating an optimal coefficient k for each number of samplings N as a graph. Because there are a plurality of the coefficients k that can acquire an almost equivalent effect to each number of samplings N as indicated in FIG. 6, the coefficients k corresponding to each minimum point are illustrated by two graphs. There is k that is a minimum value also in a region of k>3 but is not indicated in FIG. 7. An optimal k may be selected according to the system configuration requirements from among the plurality of coefficients k.

From these results, it is found that a detection error of the AD converter 0112 can be suppressed by executing sampling at a certain sampling period S from the start time of a measurement period TL to the (N−1)-th sampling and the N-th sampling (S039) at the same time as when the measurement period TL ends and at a timing when a time interval SL between the (N−1)-th sampling and the N-th sampling is equal to the sampling period S multiplied by a predetermined coefficient k (SL=k*S).

At this time, it is found that k is set to M+0.3 to M+0.5 in a state where M is a non-negative integer, i.e. a half-integer multiple that is non-negative from FIGS. 6 and 7.

Here, described will be the detailed configuration and the operations of the AD conversion system of FIG. 3 in the first embodiment. The AD conversion system shows a case of converting into (detecting) a digital signal using, for example, an analog voltage signal to be output from a photodiode 011a (including an electrostatic capacity 012a) in n channels of an X-ray detector of an X-ray CT apparatus as an input voltage and a view interval of the X-ray CT apparatus as a measurement period TL. However, the AD conversion system of the first embodiment is not limited to that for the X-ray CT apparatus.

The AD conversion system of FIG. 3 is configured by comprising switches 013, 016, and 017, an amplification circuit (an integral circuit or an integral amplification circuit) 014, an isolation switch 0115, a feedback capacitor 015, a reference voltage source 018, a comparator 0110, a sample hold circuit 019, a multiplexer 0111, the AD converter 0112, the sampling timing adjustment circuit 0113 that is a timing circuit, a comparator 0110 configuring a reset circuit together with the sampling timing adjustment circuit 0113, and a sample reconstruction circuit 0114. The multiplexer 0111, the AD converter 0112, the sampling timing adjustment circuit 0113, and the sample reconstruction circuit 0114 are commonly provided in n channels of the X-ray detector, and circuits 201 except the above are disposed for each channel of the X-ray detector.

Both polarities of the photodiode 011a and the electrostatic capacity 012a of the X-ray detector are connected to the two inputs of the amplification circuit 014 via the switch 013. On the other hand, the isolation switch 0115 is connected to the output of the amplification circuit 014. The feedback capacitor 015 is connected between one of the inputs of the amplification circuit 014 and the output of the amplification circuit 014 connected to the isolation switch 0115. The reference voltage source 018 is connected to both polarities of the feedback capacitor 015 via each of the switches 016 and 017.

An output signal VINT of the amplification circuit 014 is input to the AD converter 0112 via the isolation switch 0115, the sample hold circuit 019, and the multiplexer 0111. The output signal VINT of the amplification circuit 014 is input to also to the comparator 0110.

The sampling timing adjustment circuit 0113 generates a signal SAMPLE instructing a sampling timing to input to the AD converter 0112, the sample reconstruction circuit 0114, and the comparator 0110. The sampling timing adjustment circuit 0113 also generates an output signal HOLD to input to the sample hold circuit 019 and the isolation switch 013.

Figure 8:
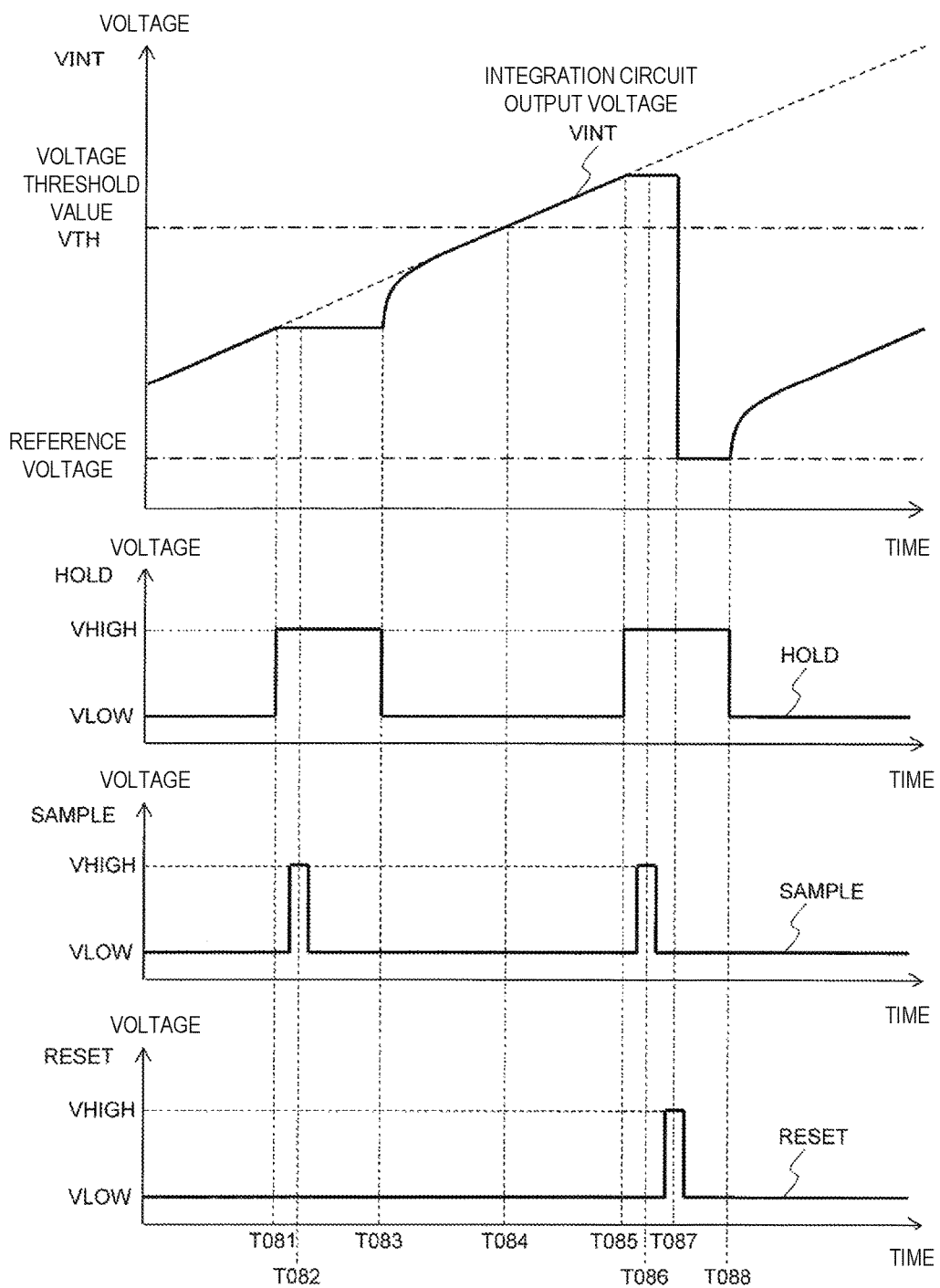
FIG. 8 is a graph illustrating an output signal of each circuit in the AD conversion system of the first embodiment.

Next, operations of the AD conversion system of FIG. 3 will be described using FIG. 8.

An electric charge is from the photodiode 011a of the X-ray detector is input to an integral circuit 014 and is integrated. As illustrated in FIG. 8, an output VINT of the integral circuit 014 is increased as time elapses by the electric charge to be supplied from the photodiode 011a. The output VINT of the integral circuit 014 is input to the AD converter 0112 via the sample hold circuit 019 and the multiplexer 0111.

The AD converter 0112 samples output of the integral circuit 014 at a timing (time T082 or T086 of FIG. 8) of the signal SAMPLE to be output from the sampling timing adjustment circuit 0113 in order to convert into a digital signal and output to the sample reconstruction circuit 0114.

Capacitor noise of the feedback capacitor 015 is suppressed during sampling by the AD converter 0112, and a signal HOLD of the sampling timing adjustment circuit 0113 becomes the VHIGH level in the sampling period and the previous and subsequent periods (time T081 to T083 or T085 to T088) in order to suppress the electric charge loss from the photodiode 011a. During the sampling by the AD converter 0112 and the previous and subsequent periods, the isolation switch 013 is isolated by the signal HOLD in order to suppress the electric charge loss from the photodiode 011a. The sample hold circuit 019 is in a hold state, and the input to the AD converter 0112 is also held. Hence, capacitor noise of the feedback capacitor 015 is suppressed.

The output VINT of the integral circuit 014 is input also to the comparator 0110. A voltage VTH equivalent to a predetermined threshold value voltage (V022) is input to the comparator 0110 from a reference voltage generation source that is not illustrated in the diagram. The signal SAMPLE is input also to the comparator from the sampling timing adjustment circuit 0113. The comparator 0110 compares the output voltage VINT of the integral circuit 014 to the voltage VTH (threshold value voltage (V022)) and allows a signal RESET to transition in the order of VLOW->VHIGH->VLOW before the output in a case where the output voltage VINT exceeds the voltage threshold value VTH (T084 of FIG. 8) in the immediately after period where the signal HOLD is at a VHIGH level (T085 to T088) in a case where the signal SAMPLE transitions in the order of VLOW->VHIGH->VLOW (T086) at a slightly later timing (T087). A comparator circuit 0110 outputs a signal RESETB that is a signal complementary to the signal RESET.

The switches 016 and 017 are closed by the signal RESET (VHIGH) output from the comparator 0110, and the feedback capacitor 015 is connected to the reference voltage 018. Hence, the output of the integral circuit 014 is reduced to a reset voltage (reference voltage) V021 and is reset. The isolation switch 0115 is released by the signal RESETB at the same time as the reset of the integral circuit 014, and the isolation switch 013 is released by that the signal HOLD becomes VLOW.

The sample reconstruction circuit 0114 adds a voltage value acquired in the final sampling to a result in which the number of times of the signal RESET in a measurement period TL was multiplied by a difference between a threshold value voltage V022 (VTH) and a reset voltage V021 (reference voltage). Hence, a voltage value (digital signal) detected in the measurement period TL is output from the sample reconstruction circuit 0114.

Next, described will be operations in which the sampling timing adjustment circuit 0113 generates the signal SAMPLE that instructing to perform sampling at a predetermined timing. In the first embodiment, as described above, the sampling timing adjustment circuit (timing circuit) 0113 outputs the signal SAMPLE so as to execute sampling at a certain sampling period S from the start time of a measurement period TL to the (N−1)-th sampling and outputs the signal SAMPLE at the same time as when the N-th sampling ends at the same time as when the measurement period TL ends and at a timing when a time interval SL between the (N−1)-th sampling and the N-th sampling is equal to the sampling period S multiplied by a predetermined coefficient k. The coefficient k is a value evaluated previously according to the number of samplings N.

Figure 9:
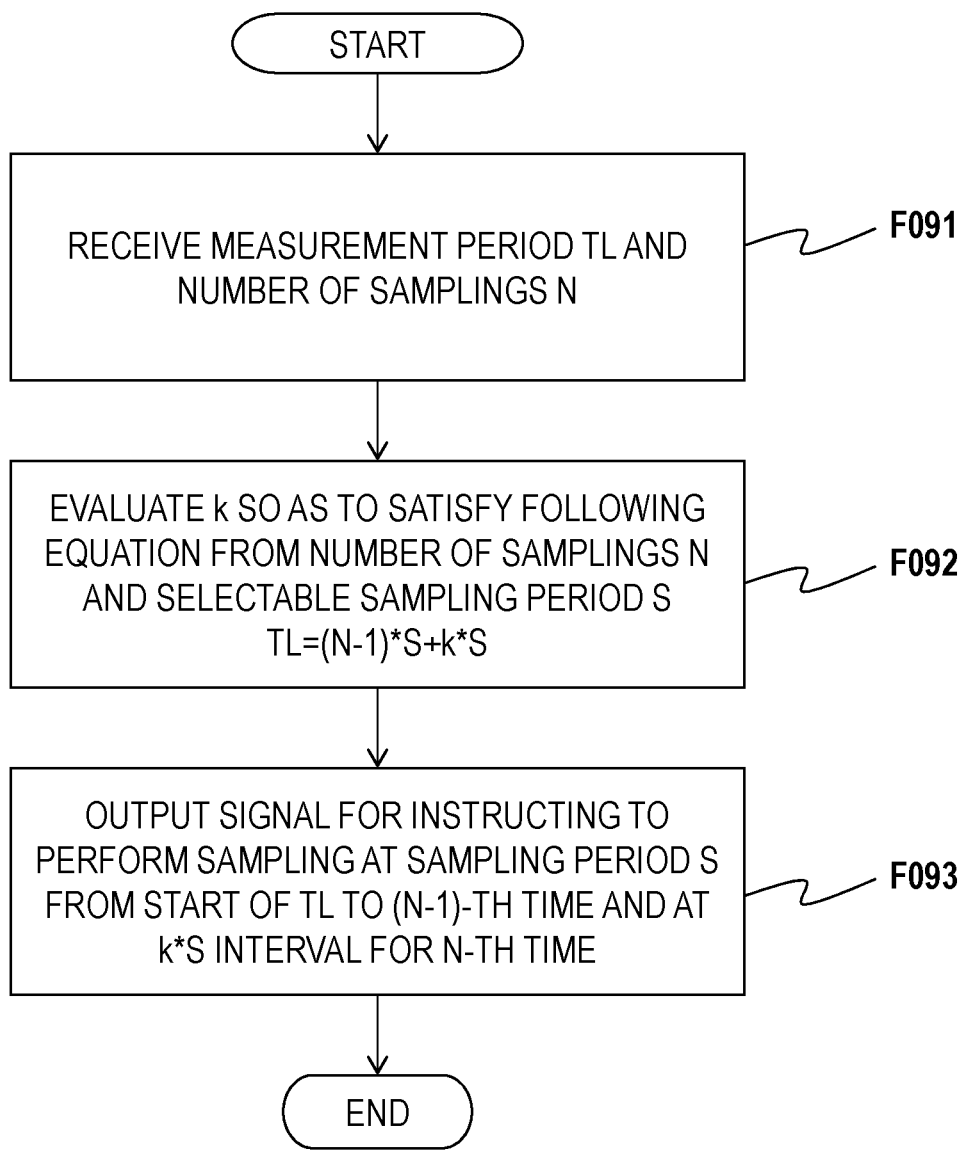
FIG. 9 is a flow chart showing operations of a sampling timing adjustment circuit 0113 of the first embodiment.

First, the sampling timing adjustment circuit 0113 receives a measurement period TL from a device (X-ray CT apparatus in this case) receiving input of an analog signal and receives the number of samplings N from an operator (Step F091 of FIG. 9). It is noted that a predetermined value can be used instead of receiving the number of samplings N from the operator. The sampling timing adjustment circuit 0113 may also receive a scanning condition (the number of views (images/scanning)) from the X-ray CT apparatus and evaluate the measurement period TL corresponding to the scanning condition.

Figure 10:
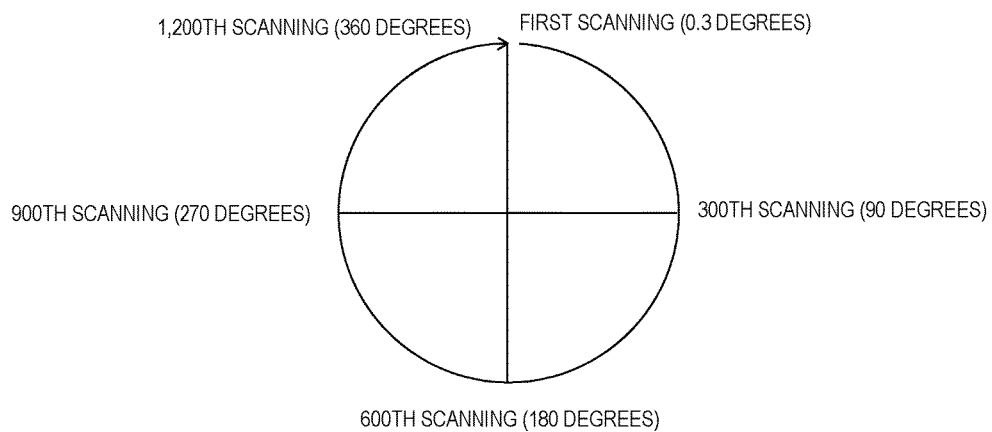
FIG. 10 illustrates a table (normal scanning: (1,200 images (views)/rotation) to be used when the sampling timing adjustment circuit 0113 of the first embodiment evaluates a measurement period (view interval).
Figure 11:
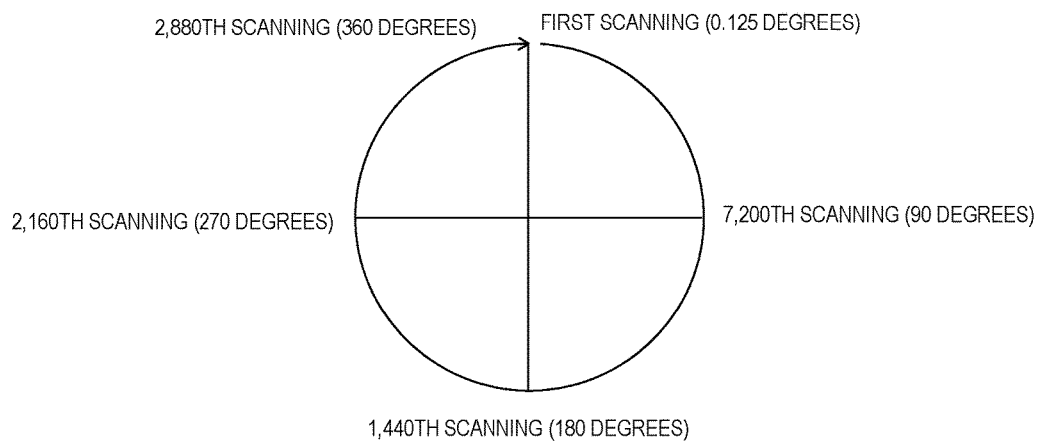
FIG. 11 illustrates a table (high-speed scanning: (2,880 images (views)/rotation) to be used when the sampling timing adjustment circuit 0113 of the first embodiment evaluates a measurement period (view interval).

Specifically, for example, as illustrated in FIGS. 10 and 11, a measurement period TL including fluctuation components corresponding to scanning conditions can be evaluated by referring to a table previously evaluated for each of the scanning conditions (such as the number of views (images/scanning)) using calculation and experiments and stored in a storage unit 0116 (FIG. 3). In this case, as illustrated in FIGS. 10 and 11, the measurement period TL for each view can be evaluated even in a case where the measurement period TL for each view is shifted from an ideal measurement period TL.

Next, the sampling timing adjustment circuit 0113 refers to a table and the like indicating a relationship between the number of samplings N, a sampling period S, and an optimal k stored in the storage unit 0116 in order to evaluate the optimal k corresponding to the number of samplings N received in Step F091 (Step F092). At this time, the sampling timing adjustment circuit 0113 is configured so as to satisfy $(N-1)*S+k*S=TL$. When there are a plurality of candidates as the sampling period S due to the characteristics of the AD converter, an optimal candidate may be selected appropriately. The sampling timing adjustment circuit 0113 outputs a signal SAMPLE instructing to perform sampling from the start of a measurement period TL for the (N-1)-th time at the sampling period S and then outputs the signal SAMPLE instructing to perform the N-th sampling at a timing when time $k*S$ elapses from the (N-1)-th sampling (Step F093).

As described above, sampling can be performed in a state where a detection error of the AD converter 0112 is suppressed in the first embodiment.

The operations of the sampling timing adjustment circuit 0113 in the flow of FIG. 9 can be realized in software by that the CPU executes a program stored in a storage unit and the like in advance and can also be realized in hardware including a programmable IC such as ASIC and FPGA.

The sampling timing adjustment circuit 0113 is configured to receive a measurement period TL from a device (the X-rat CT apparatus in this case) that receives input of analog signals or to receive scanning conditions and evaluate a measurement period TL corresponding to the scanning conditions in Step F091 of FIG. 9 in the above embodiment but is not limited to this configuration. When the measurement period TL and the scanning conditions are output from the X-ray CT apparatus, the sampling timing adjustment circuit 0113 receives them, and when not, a predetermined measurement period TL can be used. The number of samplings N is not limited similarly to the configuration in which the number of samplings N is received from an operator, and a predetermined number of samplings N can be used when the operator does not input the number of samplings N.

<<Second Embodiment>>

The AD conversion system of the second embodiment will be described.

The AD conversion system of the second embodiment can reduce a detection error of the AD converter 0112 in a case where a measurement period TL does not correspond to the sampling period S multiplied by the number of samplings N and in a case where fluctuation of the measurement period TL is sufficiently small similarly to the first embodiment. A timing circuit (sampling timing adjustment circuit) 0113 sets one or more of the N-th sampling intervals longer than the other sampling intervals when a timing for instructing to perform sampling is determined according to the length of the measurement period TL. The sampling intervals to be extended are sampling intervals in which the N-th and (N-1)-th sampling intervals were excluded at the same time as the end of the measurement period TL. The timing circuit estimates a signal value to be acquired in the next sampling for each sampling and sets sampling intervals longer when the estimated value does not exceed a maximum voltage (V022).

In the second embodiment, the sampling intervals to be extended are referred to as a sampling interval SL or an adjustment time SL, and the other sampling intervals are referred to as a sampling period S. Differing from the first embodiment, a predetermined value is used as is for the sampling period S, and the sampling period S other than SL is not changed.

The sampling timing adjustment circuit 0113 estimates an output value to be detected by the AD converter 0112 in the next sampling based on output of the AD converter 0112 acquired by sampling and inserts a sampling interval SL to be extended at a timing in which the next output value does not exceed a maximum voltage (V022). The above will be described specifically using FIG. 13 and the flow of FIG. 12.

Figure 12:
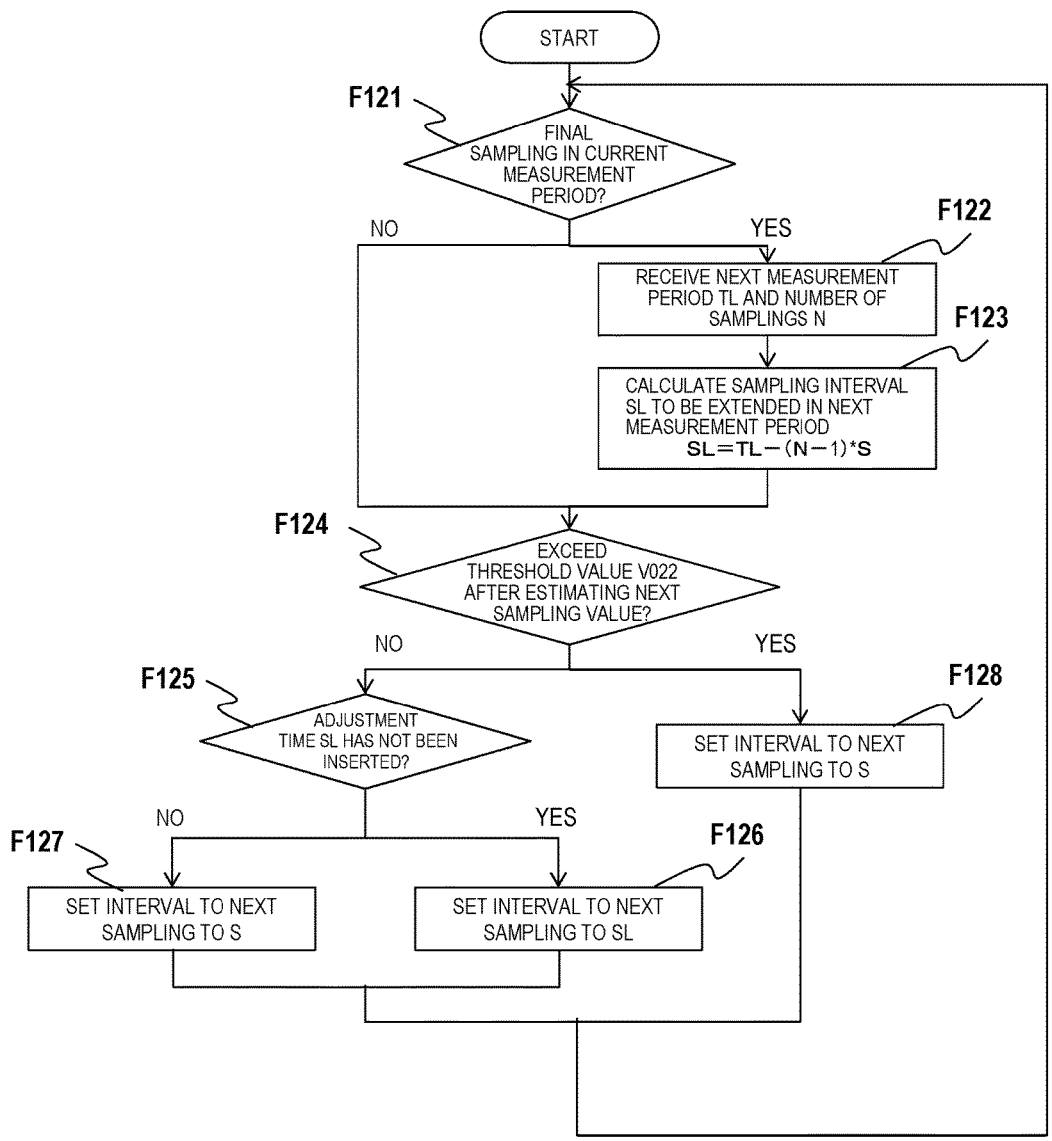
FIG. 12 is a flow chart showing operations of the sampling timing adjustment circuit 0113 of a second embodiment.

First, as illustrated in FIG. 12, the sampling timing adjustment circuit 0113 receives a length of the next measurement period TL and the number of samplings N in the final sampling in one measurement period (Steps F121 and F122). The length of the measurement period TL may be received form a device (such as an X-ray CT apparatus) that outputs analog signals, and the sampling timing adjustment circuit 0113 may calculate the length of the measurement period TL from the scanning conditions similarly to Step F091 of FIG. 9. A measurement period TL of a predetermined value can also be used. The number of samplings N is received from an operator. Alternatively, a predetermined value is used for the number of samplings N.

Next, in Step F123, the sampling timing adjustment circuit 0113 calculates a sampling interval SL to be extended in the next measurement period using the following equation:

$$SL=TL-(N-1)*3$$

TL and N are the measurement period TL received in Step F122 and the number of samplings N. S is a predetermined sampling period. Therefore, sampling can be performed using the AD converter 0112 by extending one sampling interval SL also in a case where the measurement period TL does not correspond to S multiplied by N.

Figure 13:
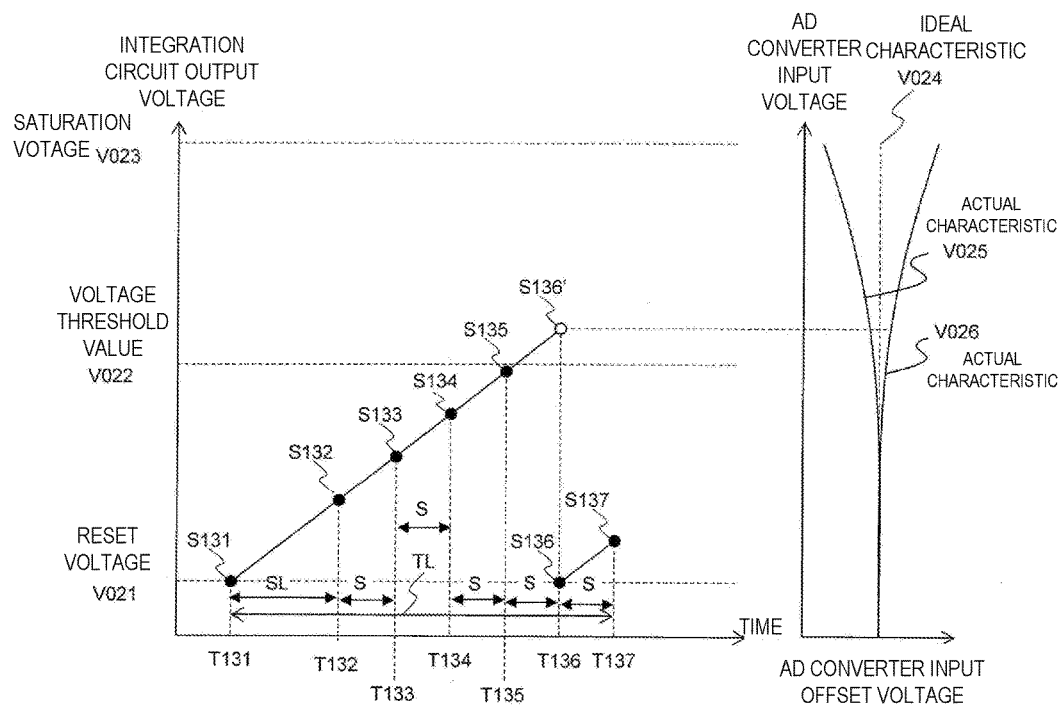
FIG. 13 illustrates sampling intervals S and SL of the AD conversion system of the second embodiment.

Next, in Step F124, the sampling timing adjustment circuit 0113 evaluates a difference between values detected in the final sampling and the previous sampling by the AD converter 0112 and adds the difference to the detection value of the final sampling. Hence, a value to be detected by the AD converter 0112 is estimated in the next sampling. In a case where the estimated value does not exceed the threshold value V022, the procedure proceeds to Step F125, and in a case where the measurement time SL is not yet inserted in the current period TL, the procedure proceeds to Step F126. In Step F126, an interval to the next sampling is extended to SL. Hence, as illustrated in FIG. 13, the first sampling interval in the current measurement period TL is an adjustment time SL.

In a case where the adjsutment time SL has been inserted in the current measurement period in Step F125, the procedure proceeds to Step F127, and an interval to the next sampling is set as an unextended sampling period S.

Figure 14:
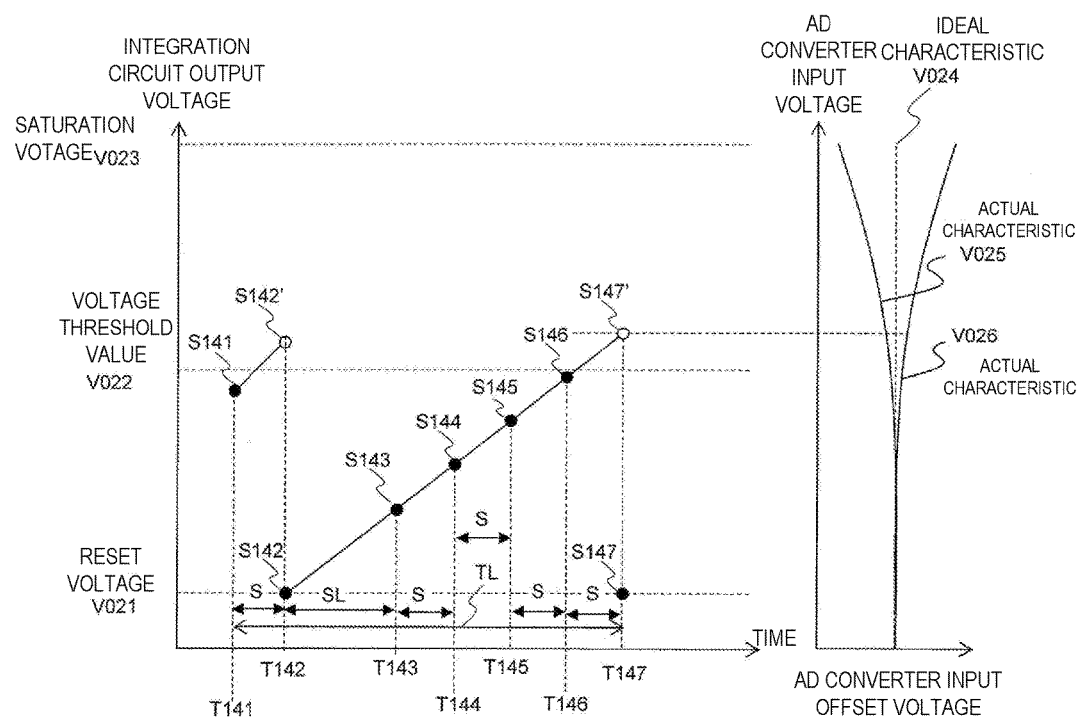
FIG. 14 illustrates sampling intervals S and SL of the AD conversion system of the second embodiment.

On the other hand, in a case where an estimated value of the next sampling exceeds the voltage threshold value V022 in Step F124, the interval to the next sampling S142' is not extended as illustrated in FIG. 14 and is set as the sampling period S as is. This prevents the next sampling S143 from greatly exceeding the voltage threshold value V022 according to the extended sampling interval SL.

Thus, in the second embodiment, a voltage value to be detected in sampling by the AD converter 0112 is estimated in order to extend a sampling interval to SL at a timing when the voltage value does not greatly exceed the voltage threshold value V022 even in a case where a measurement period TL does not correspond to a sampling period multiplied by the number of samplings. That is, an adjustment time SL can be inserted at the top of the sampling interval of the measurement period TL as illustrated in FIG. 13 or immediately after the reset as illustrated in FIG. 14. Therefore, when one sampling interval exceeds the voltage threshold value V022, the sampling interval is a sampling period S, and a detection value of the AD converter 0112 does not greatly exceeds the voltage threshold value, which can suppress an error of the detection value.

The other configuration is similar to the first embodiment, and the description will be omitted.

<<Third Embodiment>>

The AD conversion system of the third embodiment will be described.

The AD conversion system of the third embodiment is similar to the second embodiment but randomly determines a position in which an adjustment time SL whose sampling interval was extended is inserted. This will be described using FIG. 15.

Figure 15:
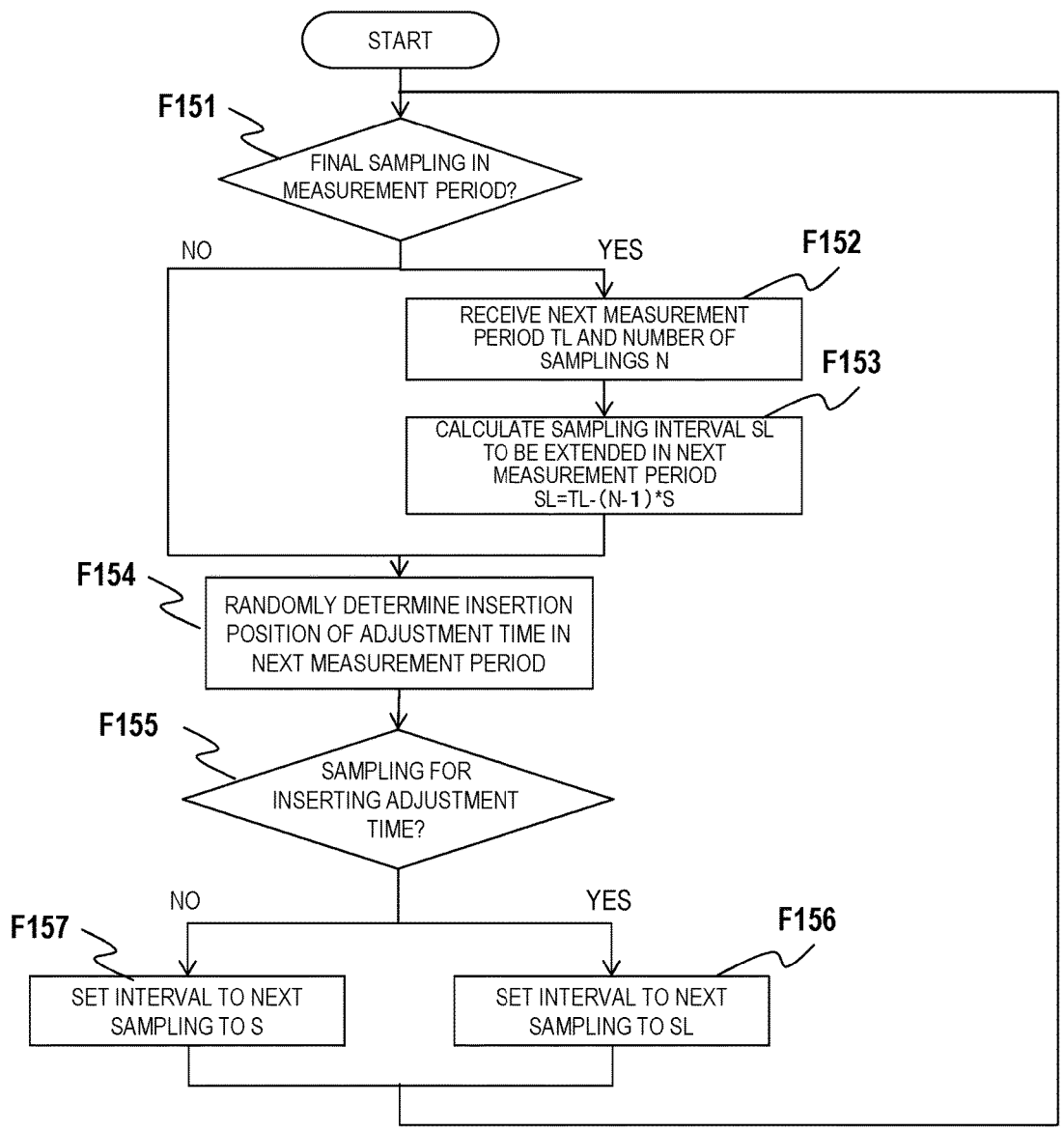
FIG. 15 is a flow chart showing operations of the sampling timing adjustment circuit 0113 of a third embodiment.

As illustrated in FIG. 15, the sampling timing adjustment circuit 0113 performs Steps F151 to F153 similarly to Steps F121 to F123 of the second embodiment and calculates an adjustment time SL whose sampling interval was extended. Then, after proceeding to Step F154, the sampling timing adjustment circuit 0113 randomly selects which sampling interval is set as the adjustment time SL from among N sampling intervals using the number of samplings N.

Figure 16:
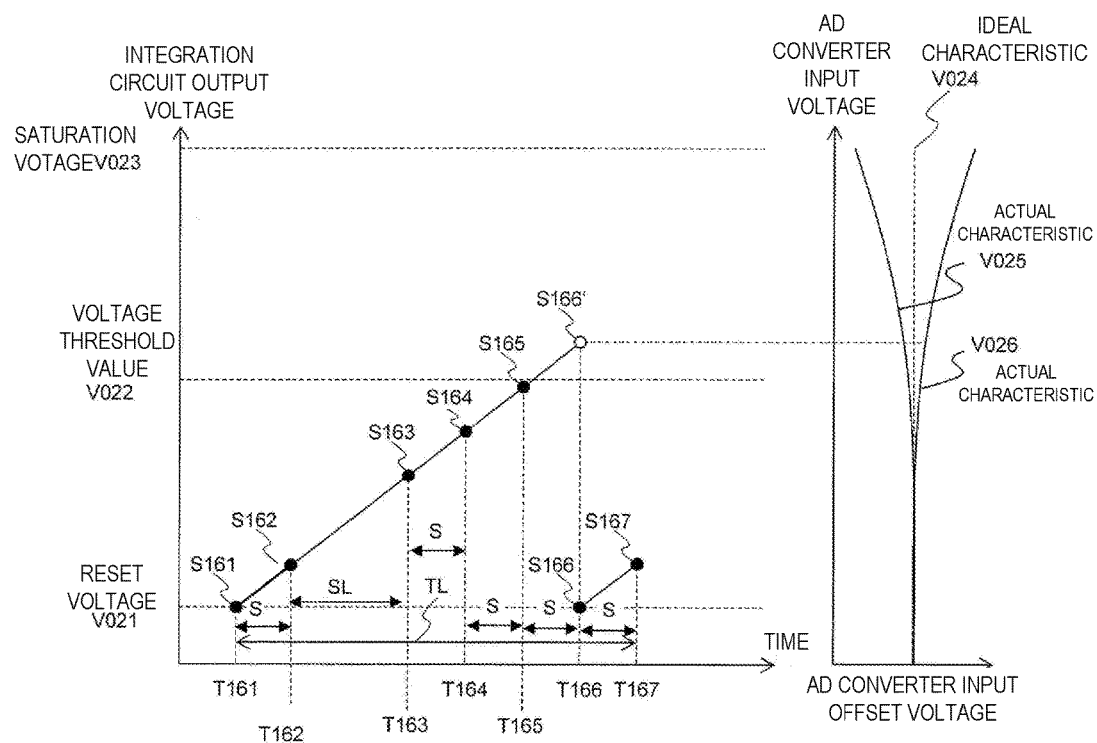
FIG. 16 illustrates sampling intervals S and SL of the AD conversion system of the third embodiment.

The sampling timing adjustment circuit 0113 outputs a signal SAMPLE instructing to perform sampling at a sampling period S until the sampling whose selected sampling interval is set as an adjustment time SL (Step F157). Then, after reaching the number of samplings of the sampling interval selected in Step F154, the signal SAMPLE that extends the sampling interval to SL and instructs to perform the sampling is output (Step F156). FIG. 16 illustrates an example of the adjustment time SL is inserted between the second sampling S162 and the third sampling S163.

Hence, an adjustment time SL can be inserted randomly, and this can reduce a possibility that a sampling interval of the adjustment time SL greatly exceeds the voltage threshold value V022 compared to a case of inserting the adjustment time SL at a predetermined timing such as a case of always setting the final sampling interval to the adjustment time SL. Therefore, a detection value error of the AD converter 0112 can be suppressed.

<<Fourth Embodiment>>

The AD conversion system of the fourth embodiment will be described.

The AD conversion system of the fourth embodiment is different from the first to third embodiments and evenly extends and contrasts N sampling intervals in order to correspond to a measurement period TL. This will be described using FIGS. 17 and 18.

Figure 17:
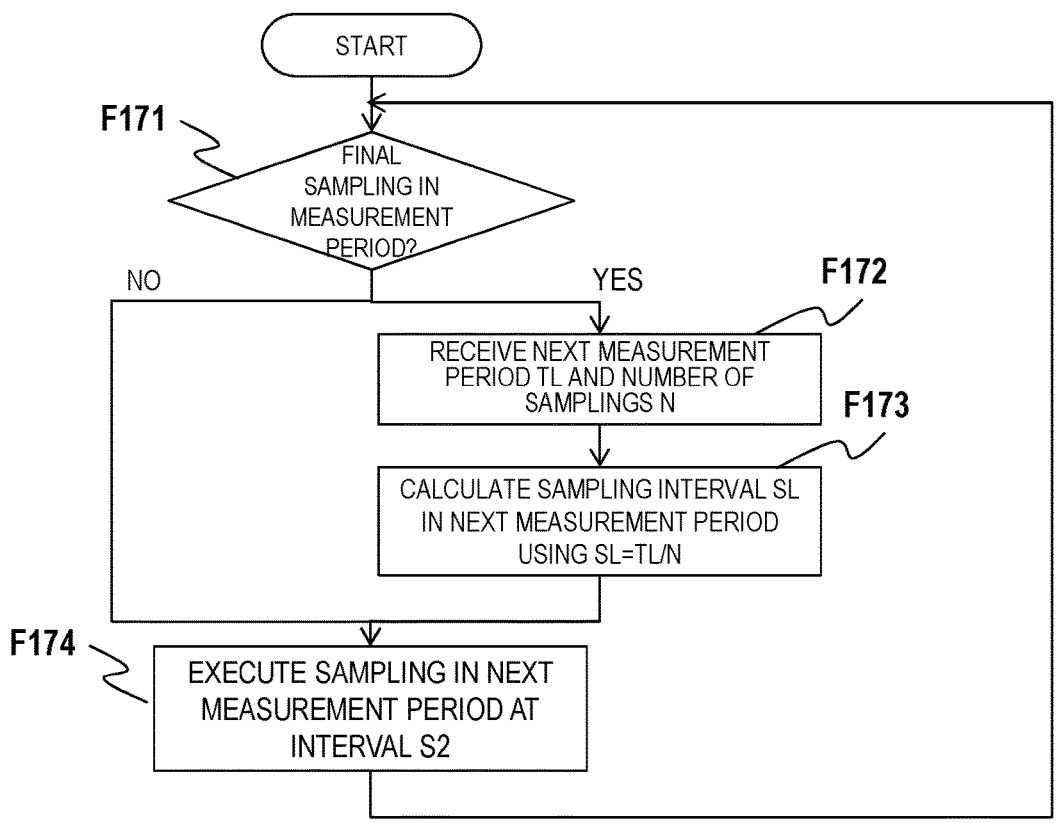
FIG. 17 is a flow chart showing operations of the sampling timing adjustment circuit 0113 of a fourth embodiment.

As illustrated in FIG. 17, the sampling timing adjustment circuit 0113 performs Steps F171 to 172 similarly to the second embodiment and receives a length TL of the next measurement period and the number of samplings N. Then, in Step F173, the sampling timing adjustment circuit 0113 calculates a sampling interval S2 in which a measurement period TL was evenly divided by N sampling intervals using the number of samplings N. A signal SAMPLE instructing to perform sampling is output at the calculated sampling interval S2 in the measurement period TL.

Figure 18:
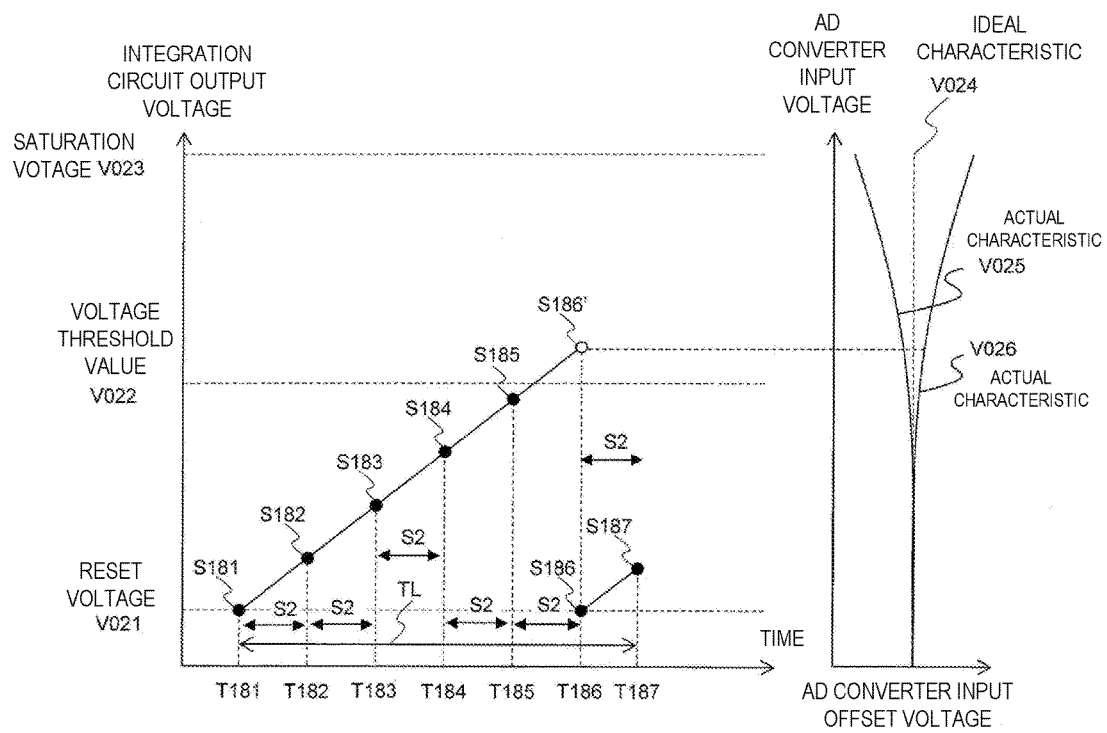
FIG. 18 illustrates a sampling interval S2 of the AD conversion system of the fourth embodiment.

Hence, as illustrated in FIG. 18, the sampling intervals S2 are greater than the sampling periods S but are less than SL when only one sampling interval is set as an adjustment time SL. Therefore, even when a sampling interval S2 exceeds the voltage threshold value 022, a detection value error of the AD converter 0112 can be suppressed more than when the adjustment time SL exceeds the voltage threshold value 022.

<<Example of Sampling Using the Embodiments>>

Figure 19:
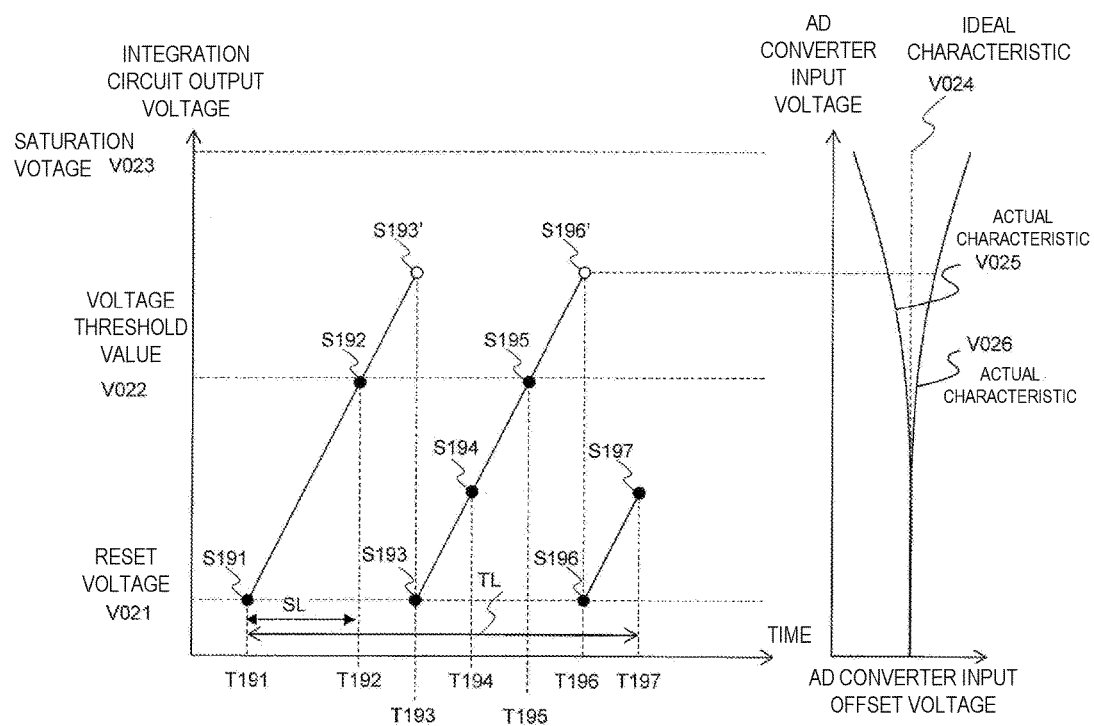
FIG. 19 illustrates an example of sampling using the second or third embodiment.

FIG. 19 illustrates an example in which an adjustment time SL is inserted in the first sampling interval (between the start of the measurement period TL and the first sampling S192) using the second or third embodiment.

Hence, the sampling intervals are not extended in the sampling intervals between S192 and S193' as well as S195 and S196' that exceed the voltage threshold value. Therefore, a detection value error of the AD converter 0112 is effectively suppressed.

Figure 20:
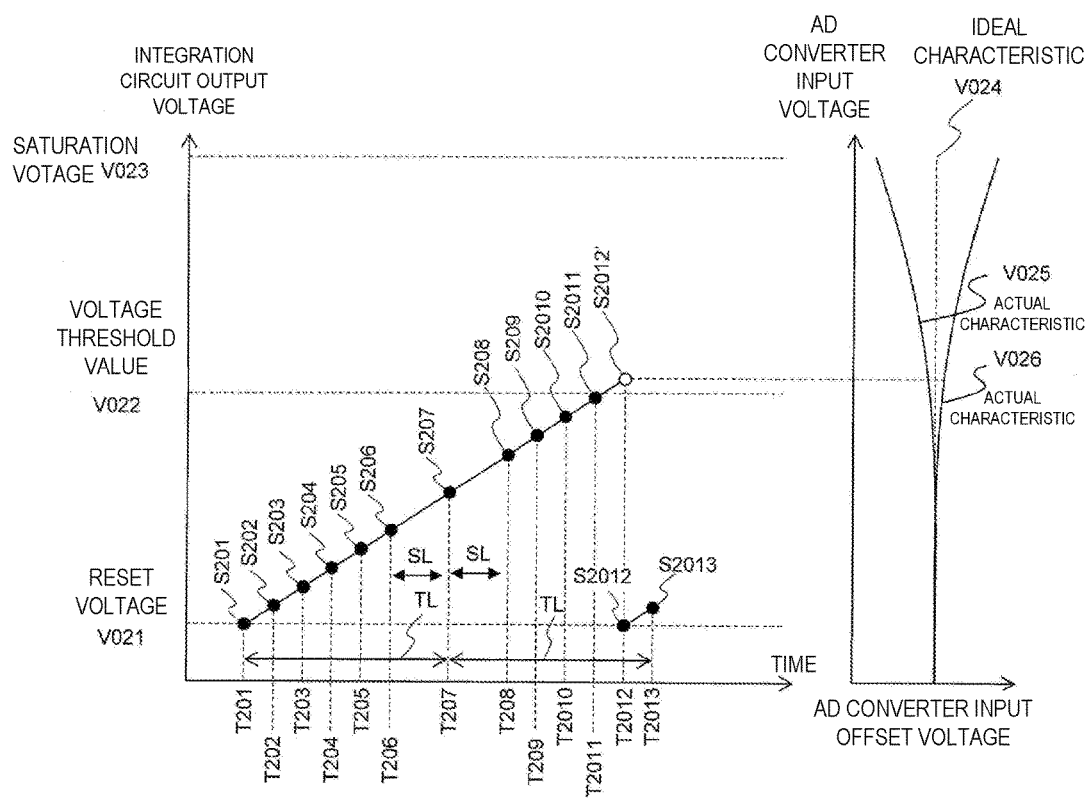
FIG. 20 illustrates an example of sampling using the second or third embodiment.

FIG. 20 illustrates an example in which the adjustment times SL are inserted in the final sampling interval of the first measurement period TL (between S206 and S207) and between the first sampling interval of the second measurement period TL (S207 and S208) using the second or third embodiment.

Hence, the sampling interval is not extended between the sampling intervals S2011 and S2012' exceeding the voltage threshold value. Therefore, a detection value error of the AD converter 0112 is effectively suppressed.

Figure 21:
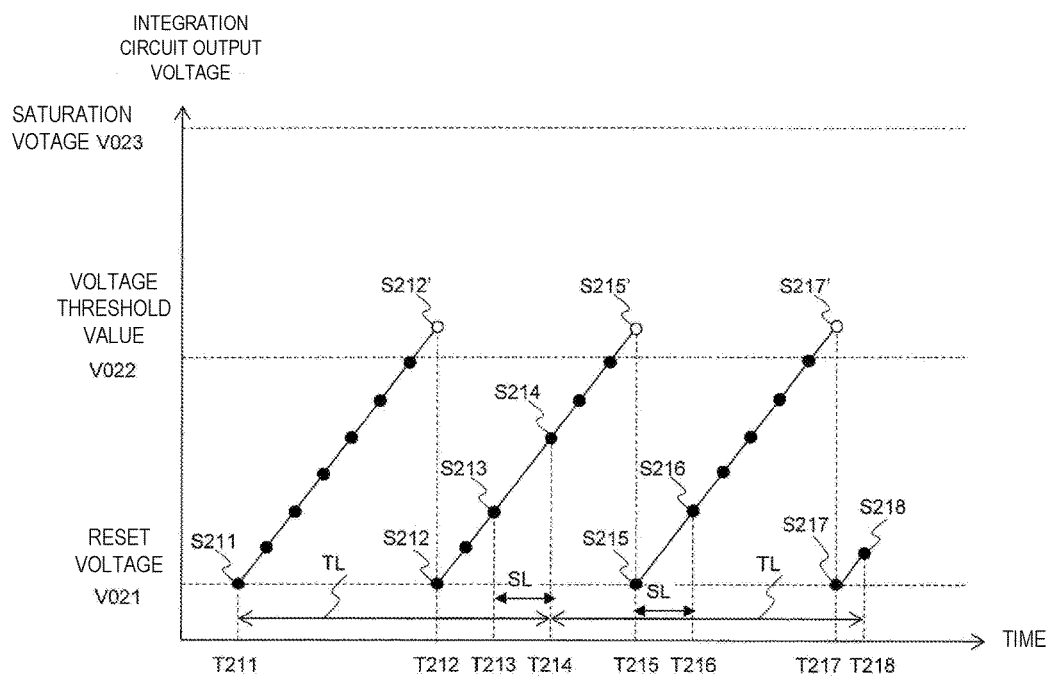
FIG. 21 illustrates an example of sampling using the second or third embodiment.

FIG. 21 illustrates an example in which the adjustment times SL are inserted in the final sampling interval of the first measurement period TL (between S213 and S214) and between the fourth sampling interval of the second measurement period TL (S215 and S216) using the second or third embodiment in case of having an input voltage that requires three resets in the two measurement periods. Thus, even when an input electric charge amount from the photodiode 011a is large in the measurement period TL, extension of the sampling intervals that exceed the voltage threshold value can be suppressed in the AD converter of the second and third embodiments, which effectively suppresses a detection value error of the AD converter 0112.

Figure 22:
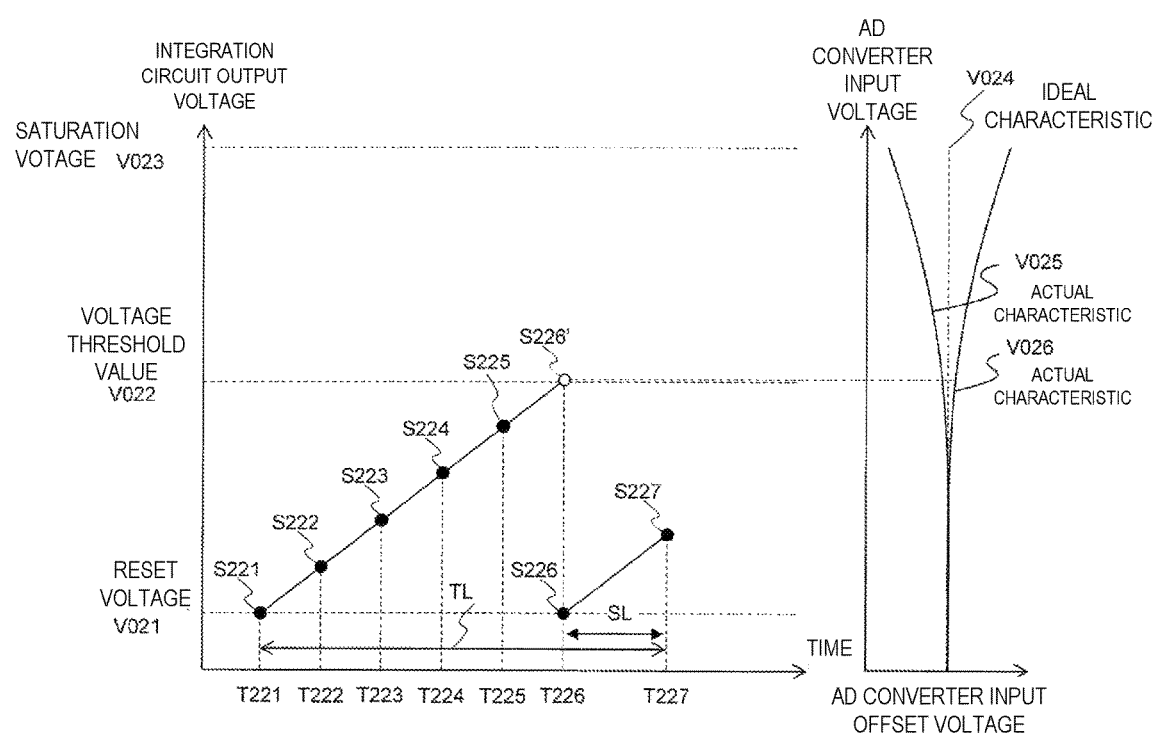
FIG. 22 illustrates an example of sampling using the second or third embodiment.

FIG. 22 illustrates an example in which the adjustment time SL is inserted in the final sampling interval (between S226 and S227) of the measurement period TL using the second or third embodiment. Because the sampling interval (between S225 and S226') exceeding the voltage threshold value is not extended, a detection value error of the AD converter 0112 is effectively suppressed.

Figure 23:
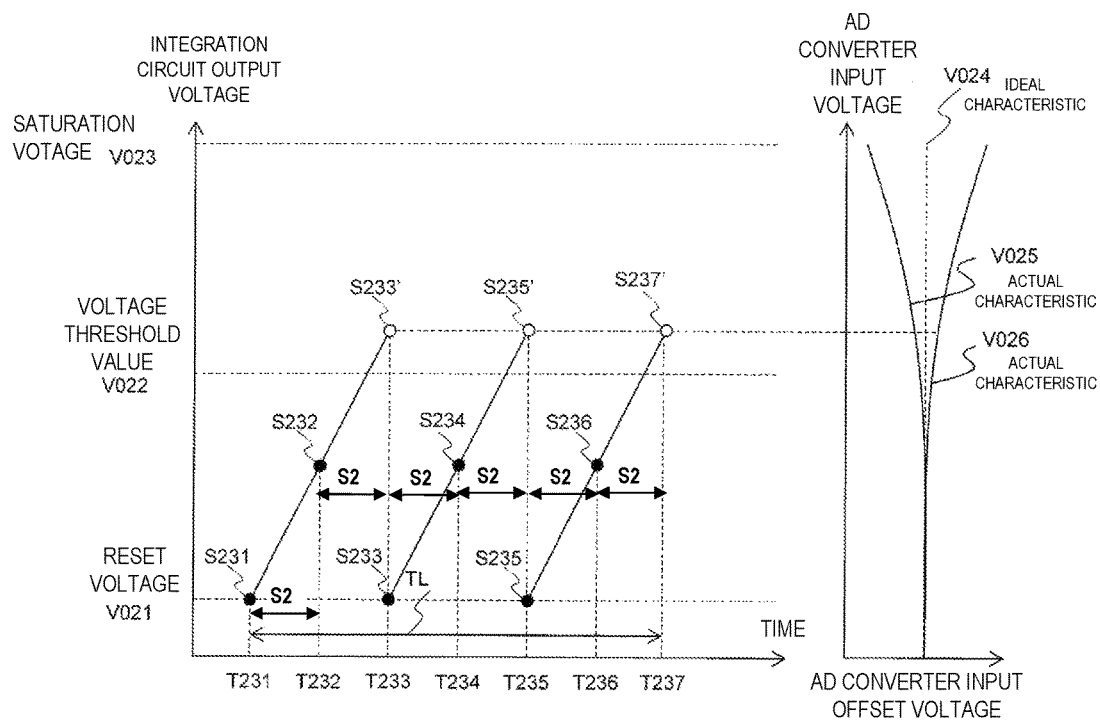
FIG. 23 illustrates an example of sampling using the fourth embodiment.

FIG. 23 illustrates an example in which the sampling intervals S2 are set at equal intervals using the fourth embodiment. FIG. 23 is an example of a large input voltage at which three resets are generated in one measurement period TL. Because the sampling intervals S2 are set at equal intervals, sampling points exceeding the voltage threshold value greatly are not generated, which suppresses a detection value error of the AD converter 0112.

<<Sampling in Comparative Example>>

Figure 24:
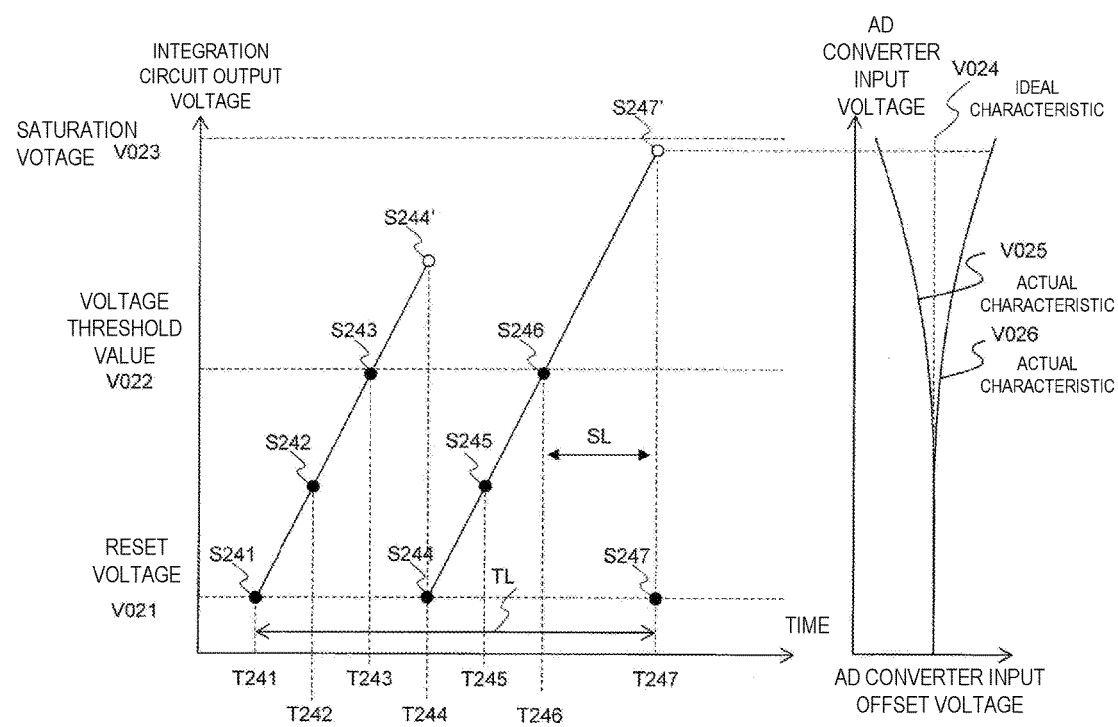
FIG. 24 illustrates an example of sampling of a comparative example.

FIG. 24 illustrates an example in which the adjustment time SL is inserted in the final sampling interval of the measurement period TL, i.e. the sampling interval exceeding the voltage threshold value V022 as a comparative example of FIGS. 19 and 23 of the present embodiment. Because the adjustment time SL is longer than the other sampling periods S, a voltage of the sampling S247' that greatly exceeds the voltage threshold value V022 is detected, and a detection error of the AD converter 0122 is large compared to FIGS. 19 and 23 of the present embodiment.

Figure 25:
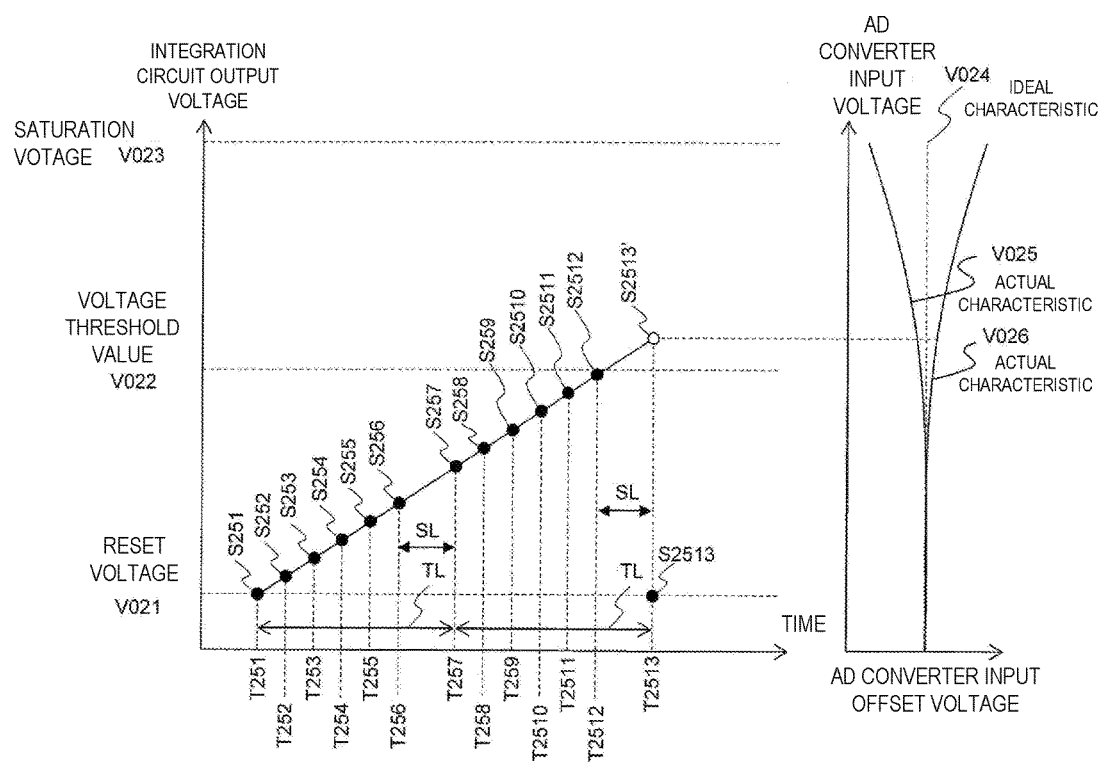
FIG. 25 illustrates an example of sampling of a comparative example.

FIG. 25 illustrates an example in which the adjustment time SL are inserted in the final sampling interval of the second measurement period TL, i.e. the sampling interval exceeding the voltage threshold value V022 as a comparative example of FIG. 20 of the present embodiment. Because the adjustment time SL is longer than the other sampling periods S, a voltage at the sampling S2513' that exceeds the voltage threshold value V022 is detected, and a detection error of the AD converter 0122 is large compared to FIG. 22 of the present embodiment.

<<Fifth Embodiment>>

Figure 26:
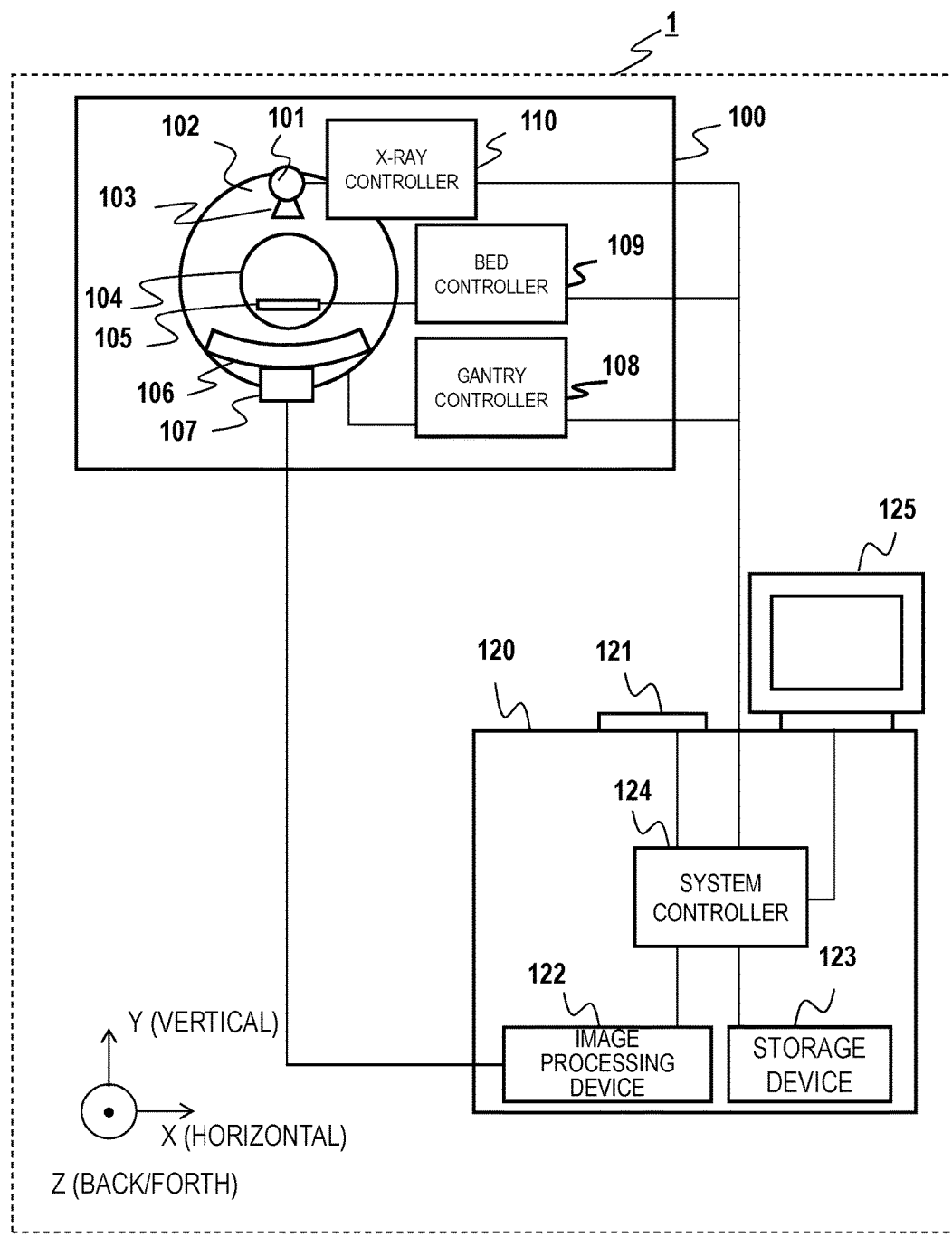
FIG. 26 is a block diagram of the X-ray CT apparatus of a fifth embodiment.

The fifth embodiment will be described using FIG. 26 in order to explain a medical image scanning apparatus that uses any of the AD conversion systems of the first to fourth embodiments. FIG. 26 describes an X-ray CT apparatus as an example.

An X-ray CT apparatus 1 is provided with a scan gantry unit 100 and an operation unit 120 as illustrated in FIG. 26.

The scan gantry unit 100 comprises an X-ray tube device 101, a rotary disk 102, a collimator 103, an X-ray detector 106, a data acquisition device 107, a bed device 105, a gantry controller 108, a bed controller 109, and an X-ray controller 110.

The X-ray tube device 101 irradiates X-rays to an object placed on the bed device 105. The collimator 103 restricts an irradiation range of the X-rays to be irradiated from the X-ray tube device 101. The rotary disk 102 is provided with an opening 104 for carrying the object placed on the bed device 105, the X-ray tube device 101, and the X-ray detector 106 and rotates around the object.

The X-ray detector 106 is disposed opposite to the X-ray tube device 101 and measures a spatial distribution of transmission X-rays by detecting X-rays transmitted through an object. The X-ray detector 106 is a device in which a lot of detection elements (channels) are one-dimensionally arranged in the rotation direction of the rotary disk 102 or in which a lot of detection elements are two-dimensionally arranged in the rotation direction of the rotary disk 102 and the rotation-axis direction.

Figure 1:
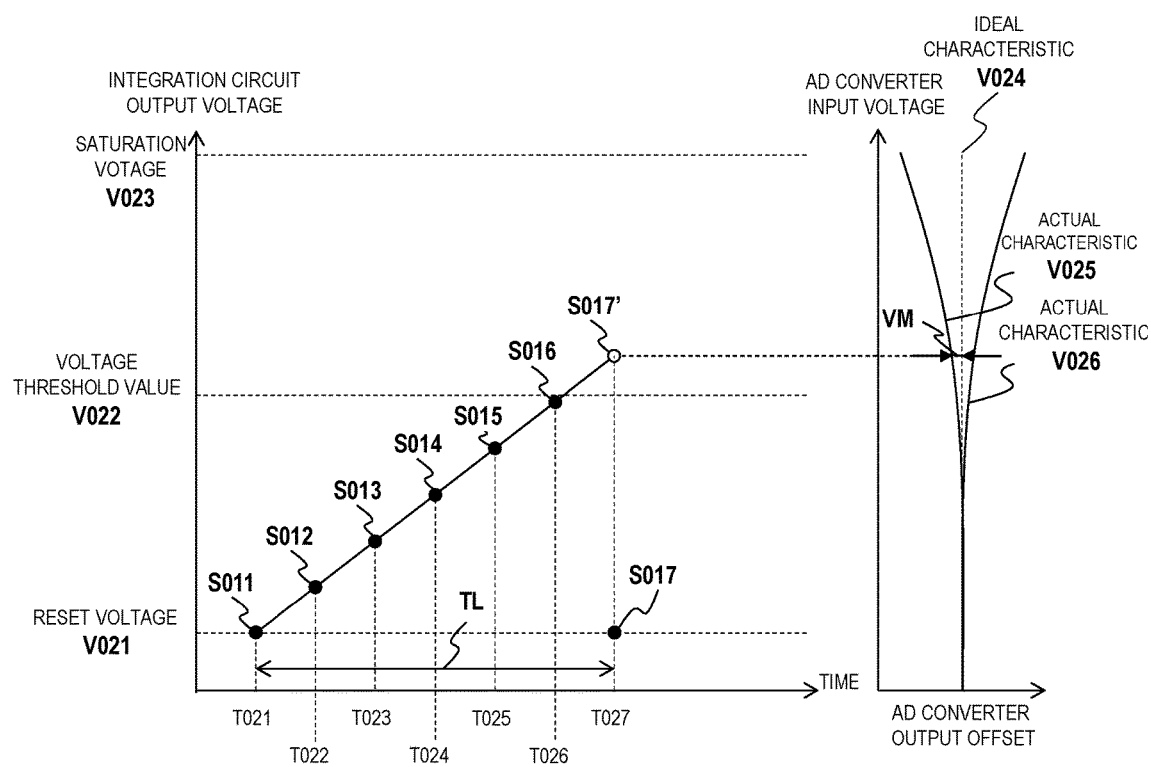
FIG. 1(a) is a graph illustrating characteristics of an input offset voltage of the AD converter.
FIG. 1(b) illustrates sampling in a measurement period TL by a conventional AD conversion system.
Figure 2:
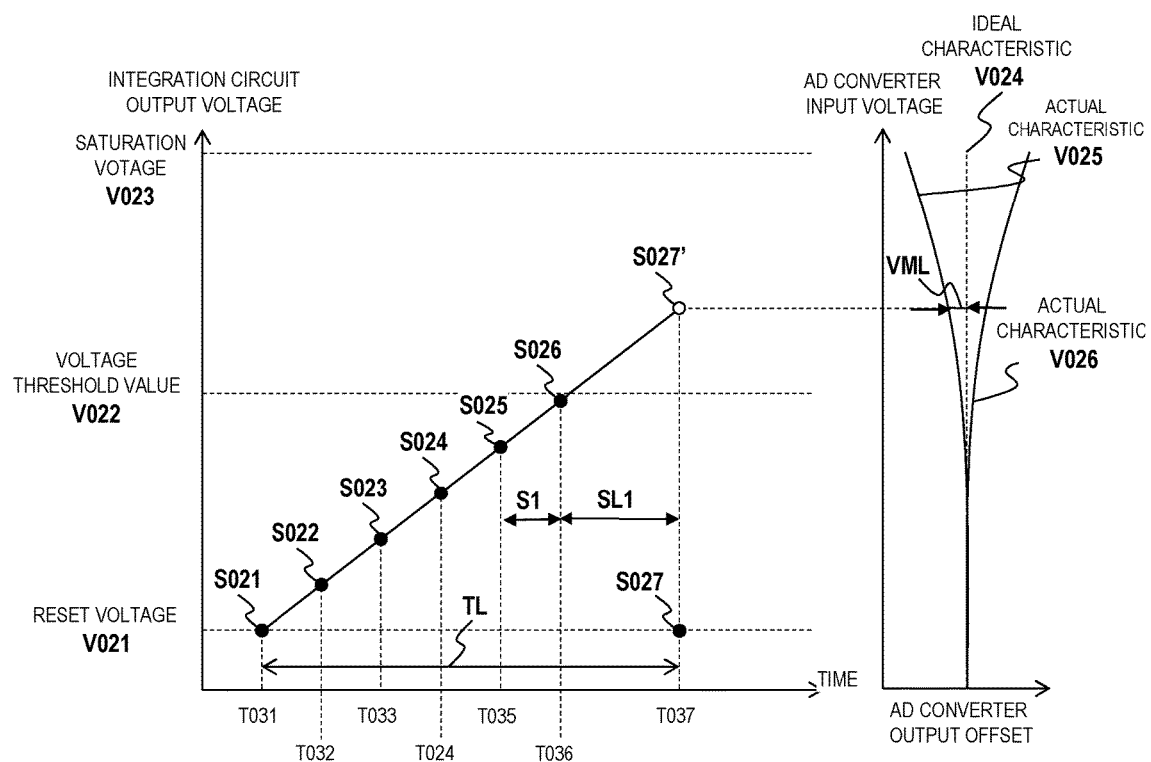
FIG. 2 illustrates a detection error VML when a sampling interval is extended in the conventional AD conversion system.

The detection elements (channels) include phosphor elements converting X-rays into light and the photodiode 011a (refer to FIG. 2) converting the light that the phosphor elements emit into electrical signals.

The data acquisition device 107 acquires an X-ray amount detected by the X-ray detector 106 as digital data. Any of the AD conversion systems of the first to fourth embodiments is mounted on the data acquisition device 107 in order to convert output of the photodiode 011a into digital signals.

The gantry controller 108 controls rotation and gradient of the rotary disk 102. The bed controller 109 controls the up-down, back-forth, and left-right movements of the bed device 105. It is noted that each direction of the up-down, back-forth, and left-right movements is indicated in FIG. 26 and that each direction is referred also to the Y direction, Z direction, and X direction in the subsequent description. The X-ray controller 110 controls electric power to be input to the X-ray tube device 101.

The operation unit 120 comprises an input device 121, an image processing device 122, a display device 125, a storage device 123, and a system controller 124. The input device 121 is a device to input object names, examination dates, scanning conditions (such as the number of views) and is specifically a keyboard, a pointing device, a touch panel, or the like. The image processing device 122 is a device to reconstruct CT images by performing calculation processing on measurement data to be sent from the data acquisition device 107. The display device 125 is a device to display CT images generated by the image processing device 122 and is specifically a CRT (Cathode-Ray Tube), a liquid crystal display, or the like. The storage device 123 is a device to store data acquired by the data acquisition device 107 and image data of the CT images and the like generated by the image processing device 122 and is specifically an HDD (Hard Disk Drive) or the like. The system controller 124 is a device to control these devices, the gantry controller 108, the bed controller 109, and the X-ray controller 110.

The X-ray controller 110 controls electric power to be input to the X-ray tube device 101 based on scanning conditions such as an X-ray tube voltage and an X-ray tube current input from the input device 121, and the X-ray tube device 101 irradiates X-rays to the object according to the scanning conditions. The X-ray detector 106 detects X-rays irradiated from the X-ray tube device 101 and transmitted through the object using a lot of X-ray detection elements and measures a distribution of the transmission X-rays. The rotary disk 102 is controlled by the gantry controller 108 and rotates based on scanning conditions including a rotational speed input from the input device 121. The bed device 105 is controlled by the bed controller 109 and operates based on scanning conditions including a helical pitch input from the input device 121.

The X-ray irradiation from the X-ray tube device 101 and the measurement of the transmission X-ray distribution by the X-ray detector 106 are repeated according to the rotation of the rotary disk 102, which obtains projection data from various angles. The projection data is associated with a view representing each angle (VIEW) and a channel (ch) number as well as a column number that are a detection element number of the X-ray detector 106. The projection data obtained from various angles are transmitted to the image processing device 122. The image processing device 122 reconstructs CT images by performing a back projection process on the projection data transmitted from various angles. The CT images obtained by the reconstruction are displayed on the display device 125.

Digital signals in which detection errors were suppressed can be obtained using the AD conversion systems of the first to fourth embodiments for the data acquisition device 107 of the X-ray CT apparatus, which can reconstruct high-resolution CT images with few artifacts.

<<Sixth Embodiment>>

Figure 27:
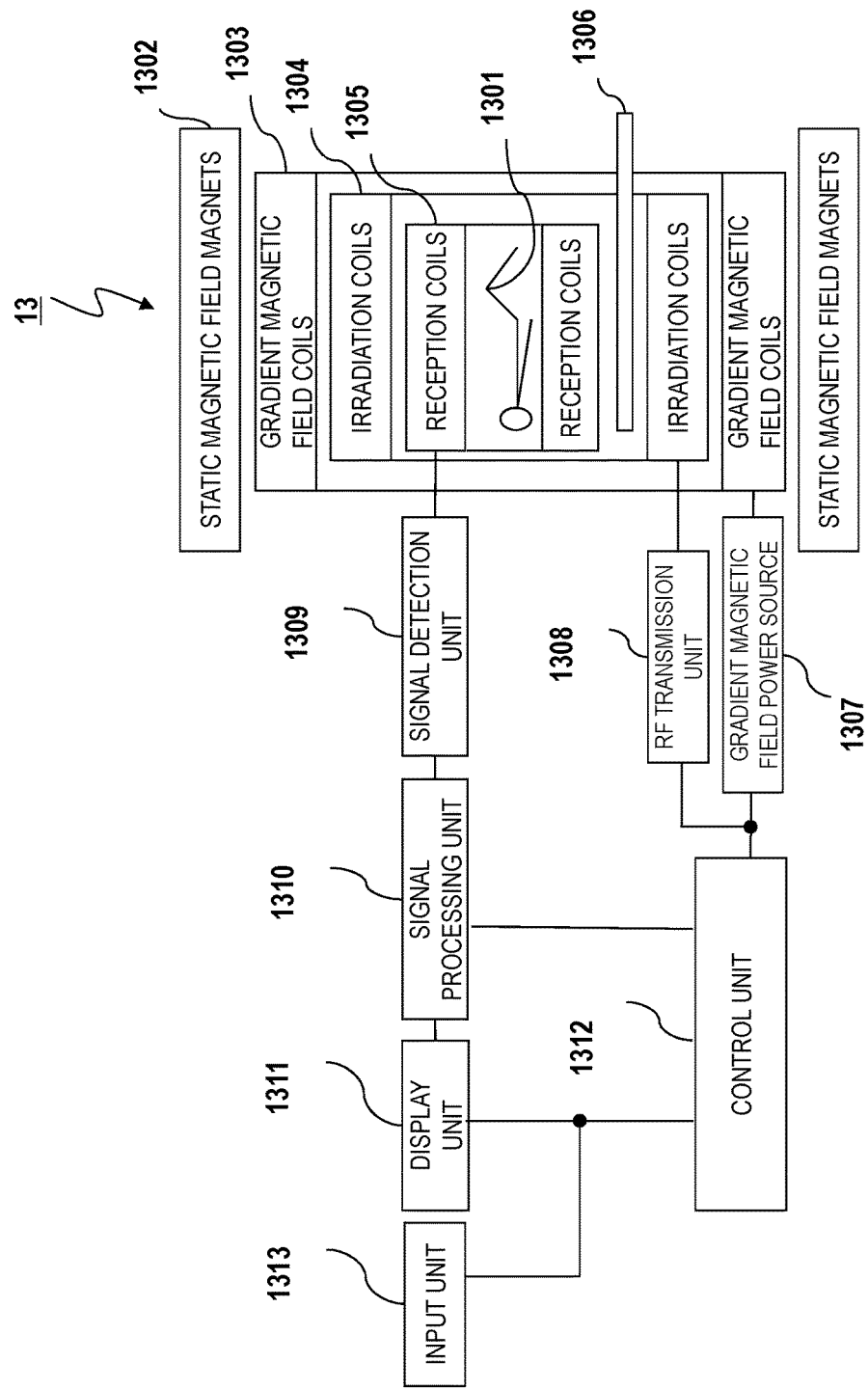
FIG. 27 is a block diagram of the MRI apparatus of a sixth embodiment.

In the sixth embodiment, an MRI apparatus is described as another example of a medical image scanning apparatus that uses any of the AD conversion systems of the first to fourth embodiments using FIG. 27.

FIG. 27 is a schematic diagram of one configuration example of the MRI apparatus. An MRI apparatus 13 comprises static magnetic field magnets 1302 generating a static magnetic field around an object 1301, gradient magnetic field coils 1303 generating a gradient magnetic field, irradiation coils 1304 irradiating high-frequency magnetic field pulses (referred also to as "RF pulses") to the object, reception coils 1305 detecting NMR signals from the object, a bed 1306 where the object 1301 lies.

The static magnetic field magnets 1302 are disposed in a wide space around the object 1301, are composed of any of a permanent magnet, a superconducting magnet, and a normal conducting magnet, and generate a homogeneous static magnetic field in a parallel or vertical direction to the body axis of the object 1301.

The gradient magnetic field coils 1303 applies a gradient magnetic field of the three-axis directions X, Y, and Z to the object 1301 according to signals from a gradient magnetic field power source 1307. Scanning cross sections of the object are set in accordance with the way of applying the gradient magnetic field The irradiation coils 1304 generate RF pulses based on signals of an RF transmission unit 1308. The atomic nucleuses of atoms constituting the biological tissue in a scanning cross section of the object 1301 set by the gradient magnetic field coils 1303 are excited by these RF pulses, which induces an NMR (Nuclear Magnetic Resonance) phenomenon.

Echo signals, which are NMR signals generated by the NMR phenomenon of the atomic nucleuses of atoms constituting the biological tissue of the object 1301 induced by the RF pulses irradiated from the irradiation coils 1304, are received by the reception coils 1305 disposed in the vicinity of the object 1301 and are converted into analog electric signals. A signal detection unit 1309 detects output of the reception coils 1305 to convert into digital signals.

Any of the AD conversion systems of the first to fourth embodiments is used for the signal detection unit 1309 in order to detected analog signals into digital signals.

Signal processing is performed on the digital signals to be output from the signal detection unit 1309 in a signal processing unit 1310, and the digital signals are converted into images. The converted images are displayed in a display unit 1311.

Parameters, such as a repetition time (TR) and an echo time (TE) required for scanning, are input to an input unit 1313 by an operator and are transmitted to and displayed on the display unit 1311. Similarly, these parameters are transmitted to a control unit 1312.

The control unit 1312 controls the gradient magnetic field power source 1307, the RF transmission unit 1308, and the signal processing unit 1310 in order to repeatedly generate RF pulses and each gradient magnetic field of a slice encode, a phase encode, and a frequency encode according to the parameters received from the input unit 1313 in a predetermined pulse sequence.

Digital signals in which detection errors were suppressed can be obtained using the AD conversion systems of the first to fourth embodiments for the signal detection unit 1309 of the MRI apparatus, which can reconstruct high-resolution MRI images with few artifacts.

<<Seventh Embodiment>>

Figure 28:
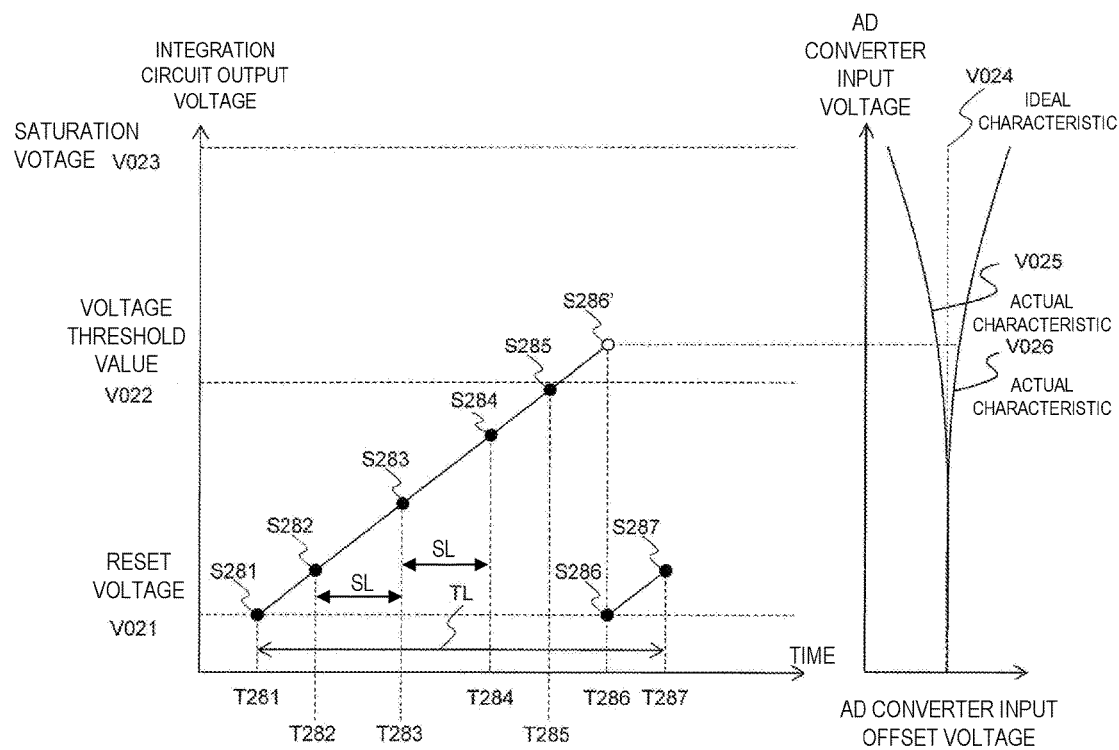
FIG. 28 illustrates an example of sampling using the seventh embodiment.

As the seventh embodiment, an example in which the adjustment time SL is disposed in a plurality of sampling intervals in the second or third embodiment is illustrated in FIG. 28. In FIG. 28, the adjustment time SL is divided and inserted in the two sampling intervals between the samplings S282 and S283 as well as the samplings S283 and S284. By thus dividing the adjustment time SL into two or more and inserting the respective adjustment times SL in the sampling intervals, fluctuation of the sampling intervals in the adjustment times SL can be suppressed, which improves the flexibility of inserting the adjustment times SL. Additionally, extension of the sampling intervals that exceed the voltage threshold value can be suppressed, which effectively suppresses a detection value error of the AD converter 0112.

REFERENCE SIGNS LIST

011a to 011a-n: photodiodes
012a to 012a-n: electrostatic capacity characteristic to the photodiodes
013: switch
014: amplification circuit
015: feedback capacitor
016: switch
017: switch
018: reference voltage source
019: sample hold circuit
0110: comparator
0111: multiplexer
0112: AD conversion circuit
0113: sampling timing adjustment circuit
0114: sample reconstruction circuit
0115: isolation switch

The invention claimed is:

1. An analog/digital conversion system comprising:
an analog/digital converter that repeats operations of sampling analog signals output from analog circuits by a number of samplings N within a specified measurement period each time the specified measurement period elapses;
a reset circuit that repeats operations of lowering an analog signal voltage to a predetermined minimum voltage to input in the analog/digital converter each time a sampled signal value exceeds a predetermined maximum voltage when the sampled signal value sampled by the analog/digital converter exceeds the predetermined maximum voltage; and
a timing circuit that instructs the analog/digital converter on a timing of sampling the analog signals,
wherein the timing circuit instructs to perform sampling at a certain sampling period S from a start time of the specified measurement period to a (N−1)-th sampling and instructs to perform a N-th sampling at a timing when a time interval between the (N−1)-th sampling and the N-th sampling is equal to the sampling period S multiplied by a predetermined coefficient k, and
wherein the predetermined coefficient k is a value evaluated previously according to the number of samplings N and is a non-integer.

2. The analog/digital conversion system according to claim 1,
wherein the predetermined coefficient k is (M+0.3)<=k<= (M+0.5) (M is a non-negative integer).

3. The analog/digital conversion system according to claim 1,
wherein the timing instructed by the timing circuit is a timing when the analog signals reach the predetermined maximum voltage between a (N−2)-th sampling and the (N−1)-th sampling.

4. The analog/digital conversion system according to claim 1,
wherein the timing circuit obtains and uses the predetermined coefficient k corresponding to the number of samplings N based on a relationship between a plurality of the number of samplings N previously evaluated and the corresponding said predetermined coefficient k.

5. An analog/digital conversion system comprising:
an analog/digital converter that repeats operations of sampling analog signals output from analog circuits by a number of samplings N within a specified measurement period each time the specified measurement period elapses;
a reset circuit that repeats operations of lowering an analog signal voltage to a predetermined minimum voltage to input in the analog/digital converter each time a sampled signal value exceeds a predetermined maximum voltage when the sampled signal value sampled by the analog/digital converter exceeds the predetermined maximum voltage; and a timing circuit that instructs the analog/digital converter on a timing of sampling the analog signals, wherein the timing circuit determines the timing according to the length of the specified measurement period, wherein the timing circuit sets one or more of N-th sampling intervals longer than other sampling intervals, and wherein the one or more of N-th sampling intervals set longer by the timing circuit are sampling intervals in which the N-th and a (N−1)-th sampling intervals are excluded.

6. An analog/digital conversion system comprising:

an analog/digital converter that repeats operations of sampling analog signals output from analog circuits by a number of samplings N within a specified measurement period each time the specified measurement period elapses;

a reset circuit that repeats operations of lowering an analog signal voltage to a predetermined minimum voltage to input in the analog/digital converter each time a sampled signal value exceeds a predetermined maximum voltage when the sampled signal value sampled by the analog/digital converter exceeds the predetermined maximum voltage; and a timing circuit that instructs the analog/digital converter on a timing of sampling the analog signals, wherein the timing circuit determines the timing according to the length of the specified measurement period, wherein the timing circuit sets one or more of N-th sampling intervals longer than other sampling intervals, and wherein the timing circuit estimates an estimated signal value to be acquired in the next sampling for each sampling, and sets the sampling intervals longer when the estimated signal value does not exceed the predetermined maximum voltage.

7. An X-ray CT apparatus comprising:

an X-ray tube that generates X-rays;

a detection circuit that detects the X-rays transmitted through an object;

a rotary disk that rotates the X-ray tube and the detection circuit around the object; and an analog/digital conversion system that converts analog signals to be output from the detection circuit into digital signals, wherein the analog/digital conversion system is the analog/digital conversion system according to claim 1, and the specified measurement period of the analog/digital conversion system corresponds to scanning time of a plurality of views into which a rotation period of the rotary disk is divided for each predetermined angle range.

8. The X-ray CT apparatus according to claim 7, wherein the timing circuit evaluates fluctuation of the specified measurement period as a fluctuating measurement period based on scanning conditions, and determines a sampling timing of the specified measurement period based on the fluctuating measurement period.

9. A medical image scanning apparatus using the analog/digital conversion system according to claim 1.

10. An X-ray CT apparatus comprising:

an X ray tube that generates X-rays;

a detection circuit that detects the X-rays transmitted through an object;

a rotary disk that rotates the X-ray tube and the detection circuit around the object; and an analog/digital conversion system that converts analog signals to be output from the detection circuit into digital signals, wherein the analog/digital conversion system is the analog/digital conversion system according to claim 5, the specified measurement period of the analog/digital conversion system corresponds to a scanning time of a plurality of views into which a rotation period of the rotary disk is divided for each predetermined angle range.

11. A medical image scanning apparatus using the analog/digital conversion system according to claim 5.

12. An X-ray CT apparatus comprising:

an X-ray tube that generates X-rays;

a detection circuit that detects the X-rays transmitted through an object;

a rotary disk that rotates the X-ray tube and detection circuit around the object; and an analog/digital conversion system that converts analog signals to be output from the detection circuit into digital signals, wherein the analog/digital conversion system is the analog/digital conversion system according to claim 6, and the specified measurement period of the analog/digital conversion system corresponds to scanning time of a plurality of views into which a rotation period of the rotary disk is divided for each predetermined angle range.

13. A medical image scanning apparatus using the analog/digital conversion system according to claim 6.

14. The X-ray CT apparatus using the analog/digital conversion system according to claim 1.

* * * * *